(12) United States Patent
Urch et al.

(10) Patent No.: US 12,376,586 B2
(45) Date of Patent: Aug. 5, 2025

(54) MICROCAPSULES COMPRISING CINMETHYLN IN THE CORE AND A POLYUREA DERIVED FROM DIPHENYLMETHANE DIISOCYANATE OR AN OLIGOMER THEREOF

(71) Applicant: BASF Agro B.V., Arnhem (NL)

(72) Inventors: Henning Urch, Limburgerhof (DE); Diana Franz, Limburgerhof (DE); Marc Nolte, Limburgerhof (DE); Gerd Kraemer, Limburgerhof (DE); Amandine Michel, Limburgerhof (DE); Klaus Kolb, Limburgerhof (DE)

(73) Assignee: BASF AGRO B.V., Arnhem (NL)

( * ) Notice: Subject to any disclaimer, the term of this patent is extended or adjusted under 35 U.S.C. 154(b) by 0 days.

(21) Appl. No.: 16/476,633

(22) PCT Filed: Jan. 10, 2018

(86) PCT No.: PCT/EP2018/050590
§ 371 (c)(1),
(2) Date: Jul. 9, 2019

(87) PCT Pub. No.: WO2018/130589
PCT Pub. Date: Jul. 19, 2018

(65) Prior Publication Data
US 2019/0364888 A1 Dec. 5, 2019

Related U.S. Application Data

(60) Provisional application No. 62/444,518, filed on Jan. 10, 2017.

(30) Foreign Application Priority Data

Jan. 27, 2017 (EP) .................... 17153595

(51) Int. Cl.
| | |
|---|---|
| *A01N 25/28* | (2006.01) |
| *A01N 25/10* | (2006.01) |
| *A01N 43/80* | (2006.01) |
| *A01N 43/82* | (2006.01) |
| *A01N 43/90* | (2006.01) |
| *C07D 493/08* | (2006.01) |
| *C08G 61/10* | (2006.01) |
| *C08L 33/10* | (2006.01) |
| *C08L 75/02* | (2006.01) |

(52) U.S. Cl.
CPC ............. *A01N 25/28* (2013.01); *A01N 25/10* (2013.01); *A01N 43/90* (2013.01); *C07D 493/08* (2013.01); *A01N 43/80* (2013.01); *A01N 43/82* (2013.01); *C08G 61/10* (2013.01); *C08L 33/10* (2013.01); *C08L 75/02* (2013.01)

(58) Field of Classification Search
None
See application file for complete search history.

(56) References Cited

U.S. PATENT DOCUMENTS

| | | | |
|---|---|---|---|
| 2008/0234131 A1 | 9/2008 | Gewehr et al. | |
| 2014/0221206 A1 | 8/2014 | Formstone et al. | |
| 2016/0192645 A1 | 7/2016 | Zhang et al. | |
| 2019/0373894 A1* | 12/2019 | Urch | A01N 25/10 |

FOREIGN PATENT DOCUMENTS

| | | |
|---|---|---|
| EP | 3 112 016 A1 | 1/2017 |
| WO | 94/13139 A1 | 6/1994 |
| WO | 2015/165834 A1 | 11/2015 |
| WO | 2017/009095 A1 | 1/2017 |
| WO | 2017/009140 A1 | 1/2017 |
| WO | 2018/104117 A1 | 6/2018 |
| WO | 2018/104118 A1 | 6/2018 |

OTHER PUBLICATIONS

International Search Report dated Feb. 20, 2019, prepared in International Application No. PCT/EP2018/050590.
International Preliminary Report on Patentability dated Mar. 28, 2019, prepared in International Application No. PCT/EP2018/050590.

\* cited by examiner

*Primary Examiner* — Sin J Lee
(74) *Attorney, Agent, or Firm* — MARSHALL, GERSTEIN & BORUN LLP

(57) ABSTRACT

The present invention relates to microcapsules comprising a core, wherein the core comprises cinmethylin, and a polyurea shell, wherein the shell comprises a polyaddition product of diphenylmethane diisocyanate or an oligomer thereof and at least one amine having at least two primary amino groups; to a composition comprising such microcapsules; to a method for preparing such microcapsules or such a composition; to a composition obtainable by said preparation method; and to the use of such microcapsules or compositions for controlling undesired vegetation.

17 Claims, 1 Drawing Sheet

MICROCAPSULES COMPRISING CINMETHYLN IN THE CORE AND A POLYUREA DERIVED FROM DIPHENYLMETHANE DIISOCYANATE OR AN OLIGOMER THEREOF

This application is a National Stage application of International Application No. PCT/EP2018/050590, filed Jan. 10, 2018, which claims the benefit of U.S. Provisional Application No. 62/444,518, filed Jan. 10, 2017. This application also claims priority under 35 U.S.C. § 119 to European Patent Application No. 17153595.8, filed Jan. 27, 2017.

The present invention relates to microcapsules comprising a core, wherein the core comprises cinmethylin, and a polyurea shell, wherein the shell comprises a polyaddition product of diphenylmethane diisocyanate or an oligomer thereof and at least one amine having at least two primary amino groups; to a composition comprising such microcapsules; to a method for preparing such microcapsules or such a composition; to a composition obtainable by said preparation method; and to the use of such microcapsules or compositions for controlling undesired vegetation.

BACKGROUND OF THE INVENTION

Cinmethylin is a selective, pre-emergence, systemic herbicide useful for the control of annual grass weeds, for example in rice. At ambient conditions it is liquid and volatile, having a vapor pressure at 20° C. of $8.1 \cdot 10^{-3}$ Pa.

Volatile pesticides constitute an environmental and health hazard. Pesticide volatilization can be defined as the movement of pesticide vapors through the air. Farm workers and bystanders can be exposed to volatile pesticides by inhaling these vapors after application has occurred. Volatile pesticides can move to neighboring areas and contaminate surrounding fields, soil, forests, plants, crops, surface water etc.

Moreover, volatility quickly reduces the concentration of the pesticide on the desired site of application, consequently precluding a long-lasting effect, and thus requires its application in rather high amounts in order to ensure a sufficient activity on-site.

Suitable pesticide formulations can lower the volatiliy of the pesticide. One suitable application form for volatile pesticides is their encapsulation into suitable materials which release the pesticide at sufficiently low rates.

WO 94/13139 describes microcapsules containing a pesticide core and a shell of polyurea, polyimide, polysulfonamide, polyester, polycarbonate or polyurethane. Inter alia, microcapsules comprising cinmethylin and a shell made of polyureas obtained by the reaction of hexamethylenediamine and PAPI® 2027 (a polymethylene polyphenylisocyanate from Dow Chemical) are described. These microcapsules are produced by an interfacial polymerization process of the polyurea wall-forming material performed in an aqueous oil-in-water emulsion of the core material containing dissolved therein a first polymer wall forming material. This first polymer wall forming material is used in a amount of from 3.5 to 21% by weight relative to the weight of the core material (e.g. an active ingredient) to be encapsulated. The aqueous phase contains a specific emulsifier which is a water-soluble random co- or terpolymer of vinylpyrrolidone. This emulsifier is said to allow the production of a composition with substantially no agglomeration of the particles and with a high concentration of the encapsulated active compound of at least 480 g per liter. These capsules have however a very low release rate of the encapsulated active compound and thus a very dissatisfactory pesticidal activity. Moreover, the mandatorily used vinylpyrrolidone co-/terpolymers are rather expensive, which is of course economically disadvantageous for mass products such as pesticide formulations, and their ecological compatibility is rather low. The preferably used quaternary copolymers are even classified as aquatoxic.

WO 2015/165834 relates to a process for producing microcapsules with a core of a water-insoluble material comprising a pesticide. Inter alia, the preparation of microcapsules comprising cinmethylin is described, the shell of which is made of polyureas obtained by the reaction of Bayhydur® XP 2547 (an anionic water-dispersible polyisocyanate based on hexamethylene diisocyanate), dicyclohexylmethane diisocyanate and a polyethyleneimine.

PCT/EP 2017/080750 describes microcapsules containing a cinmethylin core and a shell of polyurea which is the polymerization product of a tetramethylxylylene diisocyanate, optionally a cycloaliphatic diisocyanate; and an aliphatic diamine.

PCT/EP 2017/080746 describes microcapsules containing a cinmethylin core and a shell of polyurea which is the polymerization product of a tetramethylxylylene diisocyanate and a polyamine with at lest three amino groups.

However, these capsules still have no optimally balanced volatilty and release rate properties.

It was the object of the present invention to provide a cinmethylin formulation with a better balanced volatility/release profile; i.e. with a sufficiently low volatility and thus a longer lasting activity on the site of application and a reduced environmental and health hazard, and at the same time, with a release profile such that it still allows a good initial and also long-lasting biological activity of the formulation, i.e. the formulation should release cinmethylin at a sufficiently high rate to ensure a sufficient herbicidal activity, but also at such a rate that it does not constitute an environmental and health hazard or at least represents a reduced environmental and health hazard.

It was also desirable to dispense with the use/presence of the vinylpyrrolidone co- or terpolymer emulsifiers as used in WO 94/13139, also when cinmethylin is present in high concentrations.

It was surprisingly found that these objects can be reached if cinmethylin is microencapsulated into a polyurea shell based on a diphenylmethane diisocyanate or an oligomer thereof and if a specific weight ratio of cinmethylin and the polyurea material and/or the polymerized isocyanate compound is respected.

SUMMARY OF THE INVENTION

In a first aspect, the invention thus relates to microcapsules comprising a core, wherein the core comprises cinmethylin, and a shell, wherein the shell comprises a polyurea material which comprises the polyaddition product of (1) diphenylmethane diisocyanate and/or at least one oligomer thereof and (2) at least one amine having at least two primary amino groups;

where the weight ratio of cinmethylin and the polyurea material of the shell; more specifically the polyaddition product of diphenylmethane diisocyanate and/or at least one oligomer thereof and at least one amine having at least two primary amino groups, is of from 30:1 to 120:1, preferably from 40:1 to 100:1, in particular from 50:1 to 70:1, specifically from 55:1 to 65:1; and/or where the overall weight ratio of cinmethylin and the diphenylmethane diisocyanate and/or at least one oligomer thereof present in the shell in polymerized form is of from 50:1 to 150:1, preferably from 60:1 to 120:1, more preferably from 70:1 to 100:1, in particular from 75:1 to 95:1, specifically from 80:1 to 90:1.

In another aspect, the invention relates to a composition comprising such microcapsules and a dispersing medium.

In another aspect, the invention relates to a composition comprising such microcapsules, at least one further herbicide different from cinmethylin and optionally a dispersing medium.

In yet another aspect, the invention relates to a method for preparing such microcapsules or said compositions comprising polymerizing diphenylmethane diisocyanate or an oligomer thereof and at least one amine having at least two primary amino groups in the presence of cinmethylin; and to a composition obtainable by this method.

In another aspect, the invention relates to the use of the microcapsules of the invention or of the compositions of the invention for controlling undesired vegetation, and to a method for controlling undesired vegetation comprising treating the soil in which undesired vegetation is growing and/or undesired vegetation and/or cultivated plants to be protected from undesired vegetation and/or their environment with the microcapsules of the invention or the compositions of the invention.

DETAILED DESCRIPTION OF THE INVENTION

The organic moieties mentioned in the following are collective terms for individual listings of the individual group members. The prefix $C_n$-$C_m$ indicates in each case the possible number of carbon atoms in the group.

The term "$C_1$-$C_{10}$-alkyl" refers to saturated straight-chain or branched aliphatic radicals having 1 to 10 carbon atoms. Examples are methyl, ethyl, n-propyl, isopropyl, n-butyl, 1-methylpropyl (sec-butyl), 2-methylpropyl (isobutyl), 1,1-dimethylethyl (tert-butyl), n-pentyl, 1-methylbutyl, 2-methylbutyl, 3-methylbutyl, 2,2-dimethylpropyl, 1-ethylpropyl, 1,1-dimethylpropyl, 1,2-dimethylpropyl, n-hexyl, 1-methylpentyl, 2-methyl pentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl, decyl, 2-propylheptyl and structural isomers thereof.

$C_1$-$C_4$-Alkanols are methanol, ethanol, n-propanol, isopropanol, n-butanol, sec-butanol, isobutanol and tert-butanol.

$C_2$-$C_4$-Alkanediols are alkanes having 2 to 4 carbon atoms and carrying two OH groups which are not bound to the same carbon atom. Examples are ethyleneglycol (ethane-1,2-diol), propyleneglycol (propane-1,2-diol), propane-1,3-diol, butane-1,2-diol, butane-1,3-diol, butane-1,4-diol and butane-2,3-diol. $C_2$-$C_5$-Alkanediols are alkanes having 2 to 5 carbon atoms and carrying two OH groups which are not bound to the same carbon atom. Examples are those mentioned for $C_2$-$C_4$-alkanediols, and additionally pentane 1,5-diol.

$C_3$-$C_8$-Alkanetriols are alkanes having 3 to 8 carbon atoms and carrying three OH groups which are all bound to different carbon atoms. Examples are glycerol (1,2,3-propanetriol), 1,2,4-butanetriol, 1,2,3- or 1,2,6-hexanetriol, 1,2,3-heptanetriol and 1,2,3-octanetriol.

$C_{10}$-$C_{22}$ Fatty acids are aliphatic, saturated or unsaturated monocarboxylic acids with 10 to 22 carbon atoms (the carboxylic group is included in this count, where the carbon chain is mostly linear. Examples for saturated $C_{10}$-$C_{22}$ fatty acids are decanoic acid (capric acid), undecanoic acid, lauric acid, tridecanoic acid, myristic acid, pentadecanois acid, palmitic acid, heptadecanoic acid, stearic acid, nonadecanoic acid, arachidic acid, heneicosanoic acid and behenic acid. Examples for unsaturated $C_{10}$-$C_{22}$ fatty acids are myristoleic acid, palmitoleic acid, oleic acid, elaidic acid, erucic acid, linoleic acid, α- and γ-linolenic acid, and arachidonic acid.

Microcapsules are spherical objects which consist of a core and shell, i.e. a wall material surrounding the core. In the microcapsules of the invention, the core contains cinmethylin. The shell comprises a polyurea material. The microcapsules usually have a particle size in the range from 0.1 to 1000 μm, preferably from 0.5 to 100 μm, more preferably from 0.5 to 50 μm, in particular from 1 to 40 μm, very particularly from 1 to 30 μm, specifically 1 to 20 μm, very specifically 1 to 10 μm.

Unless specified otherwise, the particle sizes given above and below are the average particle diameters or average particle sizes, herein also termed $d_{50}$ value. The $d_{50}$ value is defined as the value that is above the diameters of 50% by weight of the particles and below the diameters of 50% by weight of the particles. The $d_{50}$ value can be calculated from the particle size distribution of the microcapsules. The particle size distribution of the microcapsules (i.e. the diameters) can be determined for example by conventional methods such as dynamic or static light-scattering of an aqueous dispersion of the microcapsule composition, e.g. at 25° C. and a concentration in the range of 0.1 to 1% by weight. Herein, the $d_{50}$ value is determined according to ISO 13320, Particle Size Analysis—Laser Diffraction Methods, Dec. 1, 2009.

In some instances below, the $d_{90}$ value or the $d_{10}$ value is given. The $d_{90}$ value has to be understood as the value that is not exceeded by the diameters of at least 90% by weight of the microcapsules, and the $d_{10}$ value as the value of diameters which at least 10% by weight of the microcapsules exceed. The $d_{90}$ and $d_{10}$ values, like the $d_{50}$ value, can be calculated from the particle size distribution of the microcapsules. Further details are given above. The microcapsules usually have $d_{90}$ values in the range of from 0.1 to 1000 μm, preferably from 0.5 to 100 μm, more preferably from 0.5 to 50 μm, in particular from 1 to 50 μm, very particularly from 1 to 40 μm, specifically from 1 to 30 μm, very specifically 1 to 20 μm.

The common name cinmethylin as used herein refers to the racemic mixture (±)-2-exo-(2-methylbenzyloxy)-1-methyl-4-isopropyl-7-oxabicyclo[2.2.1]heptane (also referred to as the "exo-(±)-isomers", CAS RN 87818-31-3)

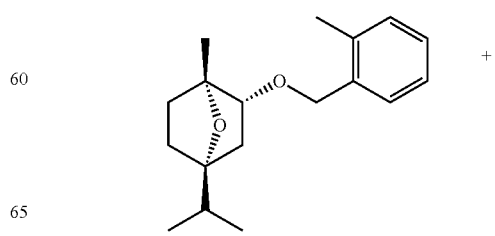

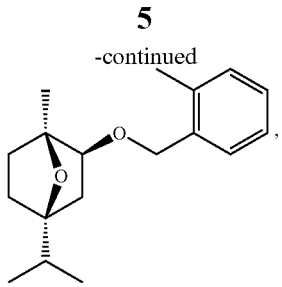

to any of its individual enantiomers or to any non-racemic mixture thereof. The racemic mixture contains equal parts of the two enantiomers (+)-2-exo-(2-methylbenzyloxy)-1-methyl-4-isopropyl-7-oxabicyclo[2.2.1]heptane (also referred to as the "exo-(+)-isomer", CAS RN 87818-61-9) and (−)-2-exo-(2-methylbenzyloxy)-1-methyl-4-isopropyl-7-oxabicyclo[2.2.1]heptane (also referred to as the "exo-(−)-isomer", CAS RN 87819-60-1). The exo-(±)-isomers, the exo-(+)-isomer and the exo-(−)-isomer including their preparation and herbicidal properties are disclosed in EP 0 081 893 A2 (see examples 29, 34, 35 and 62). Further preparation methods of these compounds are described in U.S. Pat. No. 4,487,945 (see embodiments 46 and 48). The racemic mixture (±)-2-exo-(2-methylbenzyloxy)-1-methyl-4-isopropyl-7-oxabicyclo[2.2.1]heptane is also described in The Pesticide Manual, Fourteenth Edition, Editor: C. D. S. Tomlin, British Crop Production Council, 2006, entry 157, pages 195-196 with its IUPAC name (1RS,2SR,4SR)-1,4-epoxy-p-menth-2-yl 2-methylbenzyl ether and its Chemical Abstracts name exo-(±)-1-methyl-4-(1-methylethyl)-2-[(2-methylphenyl)methoxy]-7-oxabicyclo[2.2.1]heptane. Cinmethylin is a liquid, which is barely soluble in water (0,063 g·L$^{-1}$ at 20° C.), but soluble in organic solvents. It has a boiling point of 312° C. (Pesticide Science, 1987, 21, Nr. 2, 143-153).

The microcapsules comprise a shell and a core, where the core contains cinmethylin. The core may also comprise a solvent. If this is the case, cinmethylin may be present in the core in dissolved form or as an emulsion.

"Solvent" is a liquid substance that dissolves a solute (a chemically different liquid, solid or gas), resulting in a solution. In the present context, the term "solvent" is however not restricted to a compound or medium which dissolves cinmethylin in the proper sense: This compound or medium may be more generally a dispersing medium, and thus the "solution" might be an emulsion or a solution in the proper sense (the latter being a homogeneous mixture composed of two or more substances, where the particles of the solute cannot be seen by naked eye and which does not scatter light).

Any solvent, if present in the core, is preferably selected from water immiscible organic solvents, water, water miscible organic solvents and mixtures thereof.

The solvent, if present, is preferably a water immiscible organic solvent. Water immiscible organic solvents in this context are solvents with a solubility in water at 20° C. of at most 20 g/L, preferably of at most 5 g/L and in particular of at most 0.5 g/L. Suitable examples for water immiscible organic solvents are
- a hydrocarbon solvent such a an aliphatic, cyclic and aromatic hydrocarbon (e. g. toluene, xylene, paraffin, tetrahydronaphthalene, alkylated naphthalenes or their derivatives, mineral oil fractions of medium to high boiling point (such as kerosene, diesel oil, coal tar oils));
- a vegetable oil such as corn oil, rapeseed oil;
- a fatty acid ester such as $C_1$-$C_{10}$-alkylester of a $C_{10}$-$C_{22}$-fatty acid;
- methyl- or ethyl esters of vegetable oils such as rapeseed oil methyl ester or corn oil methyl ester;
- partly saponified fats or oils; or
- rosins or rosin oils.

Mixtures of aforementioned water immiscible organic solvents are also possible. The water immiscible organic solvent is usually commercially available, such as the hydrocarbons under the tradenames Solvesso® 200, Aromatic® 200, or Caromax® 28. The aromatic hydrocarbons may be used as naphthalene depleted qualities. Preferred water immiscible organic solvents are hydrocarbons, in particular aromatic hydrocarbons.

Frequently, the water immiscible organic solvent, if present, has a boiling point above 100° C., preferably above 150° C., and in particular above 180° C.

If a water immiscible organic solvent is present in the core of the microcapsule, this is preferably comprised in an amount of up to 10% by weight, more preferably up to 5% by weight, and in particular up to 1% by weight, relative to the total weight of the core.

Preferably, the core of the microcapsule comprises less than 1% by weight, preferably less than 0.5% by weight, and in particular less than 0.1% by weight of the water immiscible organic solvent, relative to the total weight of the core.

Specifically, the core of the microcapsule is free of the water immiscible organic solvent.

Additionally or alternatively, the core of the microcapsules may comprise water, water-miscible organic solvents or mixtures thereof. Water-miscible organic solvents in this context are solvents with a solubility in water at 20° C. of more than 20 g/L. Examples for water-miscible organic solvents are $C_1$-$C_3$-alkanols, i.e. methanol, ethanol, propanol or isopropanol, polyols, such as ethylene glycol, diethylene glycol, triethylene glycol or glycerine, cyclic ethers, such as the dioxanes and tetrahydrofuran, acetone, dimethylsulfoxide, amides, such as dimethylformamide and dimethylacetamide, benzoyllactate, lactams, such as N-butylpyrrolidone and N-formylpyrrolidone, N-formylmorpholine and propylenecarbonate.

If water or a water-miscible organic solvent is present in the core of the microcapsule, this is preferably comprised in an amount of up to 10% by weight, more preferably up to 5% by weight, and in particular up to 1% by weight, relative to the total weight of the core.

Preferably, the core of the microcapsule comprises less than 1% by weight, preferably less than 0.5% by weight, and in particular less than 0.1% by weight of water and the water-miscible organic solvent, relative to the total weight of the core.

Specifically, the core of the microcapsule is free of water and the water-miscible organic solvent.

If a mixture of one or more water-immiscible organic solvents, water and/or one or more water-miscible organic solvents is present in the core of the microcapsule, these are preferably comprised in an overall amount of up to 10% by weight, more preferably up to 5% by weight, and in particular up to 1% by weight, relative to the total weight of the core.

Preferably, the core of the microcapsule comprises less than 1% by weight, preferably less than 0.5% by weight, and in particular less than 0.1% by weight of water-immiscible organic solvent, water and water miscible-organic solvent, relative to the total weight of the core.

Specifically, the core of the microcapsule is free of water-immiscible organic solvents, water and water-miscible organic solvents.

The core may optionally contain auxiliaries, such as organic modified polysiloxanes such as Break Thru S 240®; alcohol alkoxylates such as Atplus® 245, Atplus® MBA 1303, Plurafac® LF 300 and Lutensol® ON 30; EO/PO block polymers, Poloxamers, e.g. Pluronic® RPE 2035 and Genapol® B; alcohol ethoxylates such as Lutensol® XP 80; and dioctyl sulfosuccinate sodium such as Leophen® RA. If such auxiliaries are present in the core of the microcapsule, these are preferably comprised in an overall amount of up to 5% by weight, and in particular up to 1% by weight, relative to the total weight of the core.

Preferably, the core of the microcapsule comprises at least 90% by weight, more preferably at least 95% by weight, and in particular at least 99% by weight of cinmethylin, relative to the total weight of the core.

The "and/or" conjunction between the definition of the weight ratio of cinmethylin and the polyurea material and the definition of the overall weight ratio of cinmethylin and the diphenylmethane diisocyanate and/or at least one oligomer thereof means that at least one of these conditions has to be met; i.e. either the indicated weight ratio of cinmethylin and the polyurea material has to be fulfilled or the weight ratio of cinmethylin and the diphenylmethane diisocyanate and/or at least one oligomer thereof has to be fulfilled or both weight ratio conditions are fulfilled.

"Overall" weight ratio in this context means that if both diphenylmethane diisocyanate and one or more oligomers thereof, or various oligomers thereof are present in polymerized form, the weight ratio refers to the sum of the weight of all these isocyanate materials.

The weight ratio can be calculated on the basis of isocyanate material and diamine used in the production process of the microcapsules. It is assumed that nearly all, i.e. at least 90%, preferably at least 95%, of the starting material reacts. If one of the materials is used in molar excess (relative to functional groups which can react with each other; i.e. the amount of NCO groups contained in the isocyanate material and primary amino groups contained in the amine compound), e.g. the isocyanate material or the amine compound, the compound not used in excess is taken as a basis and used to calculate the reacted amount of the component used in excess. If however the isocyanate material is used in a slight excess of e.g. at most 15% or at most 10%, this excess is to be ignored since a part of the isocyanate groups reacts with water generally used in the production process (see below explanations) to amino groups which generally do not react in the polyaddition reaction unless specific conditions are met.

Alternatively, the weight ratio can be determined analytically.

In the microcapsules of the invention, the weight ratio of cinmethylin and the polyurea material comprised in the shell is preferably of from 40:1 to 100:1, in particular from 50:1 to 70:1, specifically from 55:1 to 65:1.

As the shell often consists essentially of the polyurea material, e.g. to at least 95% by weight, based on the total weight of the shell, alternatively expressed, the weight ratio of cinmethylin and the shell is preferably of from 40:1 to 100:1, in particular from 50:1 to 70:1, specifically from 55:1 to 65:1.

Additionally or alternatively the overall weight ratio of cinmethylin and the diphenylmethane diisocyanate and/or at least one oligomer thereof present in the shell in polymerized form is of from 60:1 to 120:1, preferably from 70:1 to 100:1, in particular from 75:1 to 95:1, specifically from 80:1 to 90:1.

The polyurea material is preferably based exclusively on diphenylmethane diisocyanate and/or at least one oligomer thereof as isocyanate component; i.e. no other (polymerized) isocyanate compound is present. Thus, in this case, preferably, the overall weight ratio of cinmethylin and the isocyanate material present in polymerized form in the shell is of from 60:1 to 120:1, preferably from 70:1 to 100:1, in particular from 75:1 to 95:1, specifically from 80:1 to 90:1.

To determine the amount of diphenylmethane diisocyanate and/or at least one oligomer thereof present in the shell in polymerized form and thus the weight ratio with cinmethylin, generally the amount of diphenylmethane diisocyanate and/or at least one oligomer thereof present in the shell used in the preparation of the microcapsules is taken as a basis, unless the isocyanate compound is used in large excess as compared to the amine compound. If used in large excess, the equivalent amount of the amine is taken as a basis to calculate the maximum amount of the isocyanate compound which can react in the polyaddition reaction.

Alternatively, the weight ratio can be determined analytically.

Polyurea materials are generally prepared by a polymerization process of a suitable polymer wall forming material, such as a polyisocyanate and a polyamine (in this case the polymerization process is more precisely a polyaddition process). "Polyisocyanates" contain two or more isocyanate groups. Polyisocyanates containing two isocyanate groups are also termed diisocyanates. "Polyamines" contain two or more amino groups. Polyamines suitable for the poyladdition reaction with polyisocyanates have at least two primary and/or secondary amino groups, if the latter are sufficiently reactive; preferably two primary amino groups. Polyamines containing two amino groups are also termed diamines.

In the present case, the shell of the microcapsules of the invention comprises a polyaddition product of diphenylmethane diisocyanate and/or at least one oligomer thereof and at least one amine having at least two primary amino groups.

Suitable diphenylmethane diisocyanates are diphenylmethane-4,4'-diisocyanate (4,4'-MDI), 2,4'-diphenylmethane diisocyanate (2,4'-MDI) or 2,2'-diphenylmethane diisocyanate (2,2'-MDI), and in particular diphenylmethane-4,4'-diisocyanate (4,4'-MDI) or 2,4'-diphenylmethane diisocyanate (2,4'-MDI). Preference is given to diphenylmethane-4,4'-diisocyanate (MDI), which has the formula

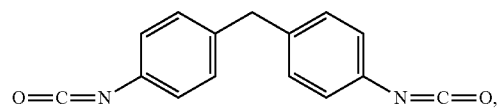 [SMILES: O=C=Nc1ccc(Cc2ccc(N=C=O)cc2)cc1]

and to mixtures comprising diphenylmethane-4,4'-diisocyanate (4,4'-MDI) and 2,4'-diphenylmethane diisocyanate (2,4'-MDI) or 2,2'-diphenylmethane diisocyanate (2,2'-MDI) or both 2,4'-MDI and 2,2'-MDI, preferably comprising diphenylmethane-4,4'-diisocyanate (4,4'-MDI) and 2,4'-diphenylmethane diisocyanate (2,4'-MDI). In some instances, in such mixtures of 2,4'-MDI and 4,4'-MDI, diphenylmethane-4,4'-diisocyanate (4,4'-MDI) can make up at least 70% by weight, preferably at least 80% by weight, in particular at least 90% by weight, and especially at least 95% by weight of the total weight of this mixture.

"Oligomers of diphenylmethane diisocyanate" are actually isocyanatophenylmethyl oligomers containing at least three phenyl rings carrying each an isocyanato group and bound to each other via a methylene bridge; i.e. in contrast to what the name suggests they can also contain an odd number of phenyl rings (carrying each an isocyanato group, of course). They can be represented by following formula:

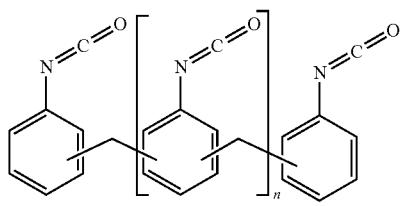

where n ranges from 1 to higher numbers, generally from 1 to 10, e.g. from 1 to 6 or from 1 to 4.

The oligomers can however also be present in condensed form, for instance as carbodiimides or uretonimines, or also in cyclic addition form, like isocyanurates. Preferably, however, they take essentially the form of the above-depicted formula.

Suitable oligomers are for example trimers (n=1) having three phenyl rings and three isocyanate groups, tetramers (n=2) having four phenyl rings and four isocyanate groups, pentamers (n=3) having five phenyl rings and five isocyanate groups or hexamers (n=4) having six phenyl rings and six isocyanate groups. Suitable are also mixtures of such oligomers or mixtures of one or more of these oligomers with "monomeric" diphenylmethane diisocyanate.

The oligomers of diphenylmethane diisocyanates are generally used as a mixture of various oligomers of the above formula with different n values. These mixtures may also contain various degrees of "monomeric" diphenylmethane diisocyanate. Such mixtures have an average NCO functionality which is generally in the range of from 2.0 to 4.0, preferably from 2.1 to 3.2, more preferably from 2.3 to 3.0, in particular from 2.5 to 2.9 and specifically about 2.7. The term "about" includes determination errors of the functionality.

Functionality means number of NCO functional groups per molecule.

The NCO content may be determined according to ASTM D 5155-96 A.

Typically, suitable oligomers of diphenylmethane diisocyanates have a viscosity (determined according to DIN 53018; 25° C.) in the range from 20 to 1000 mPa·s, more preferably from 80 to 500 mPa·s and especially from 150 to 320 mPa·s.

The oligomers are generally formed in the production process of diphenylmethane diisocyanates. For instance, the reaction of aniline and formaldehyde in the presence of HCl as a catalyst leads to a complex mixture of polyamines, including diphenylmethane diamines. This mixture is treated with phosgene, whereupon not only diphenylmethane diisocyanates are formed, but also oligomers containing three or more isocyanatophenyl rings. If desired, these can be separated from the monomeric diphenylmethane diisocyanates by a distillation step.

Preference is given to the use of oligomers of diphenylmethane diisocyanates or to the use of mixtures thereof with ("monomeric") diphenylmethane diisocyanates, since such oligomers, in contrast to diphenylmethane diisocyanates, have crosslinking properties and thus enhance the density and stability of the shell wall.

Thus, in a preferred embodiment, the shell of the microcapsules of the invention comprises a polyaddition product of at least one oligomer of the above formula wherein n is from 1 to 10, preferably 1 to 6 or 1 to 4, optionally in admixture with diphenylmethane diisocyanate, optionally preferably in admixture with diphenylmethane-4,4'-diisocyanate, diphenylmethane-2,4'-diisocyanate and/or diphenyl methane-2,2'-diisocyanate; optionally in particular in admixture with diphenylmethane-4,4'-diisocyanate or in admixture with a mixture comprising diphenylmethane-4,4'-diisocyanate and diphenylmethane-2,4'-diisocyanate; and at least one amine having at least two primary amino groups.

In some instances, in this mixture of 4,4'-MDI and 2,4'-MDI diphenylmethane-4,4'-diisocyanate can be present in an amount of at least 70% by weight, preferably of at least 80% by weight, in particular of at least 90% by weight, and especially of at least 95% by weight, based on the total weight of this mixture.

One particular example of a suitable mixture of oligomers of diphenylmethane diisocyanates and "monomeric" diphenylmethane diisocyanates is so-called polymeric diphenylmethane diisocyanate (polymeric MDI; PM DI). In contrast to what its name suggests, this is not a polymer, but a mixture of diphenylmethane diisocyanate, in particular of diphenylmethane-4,4'-diisocyanate and/or di phenyl methane-2,4'-diisocyanate, with various higher homologs ("diphenyl methane diisocyanate oligomers") with generally up to six phenyl rings each carrying an isocyanate group. Higher oligomers can also be present, but are generally contained in only negligible amounts. A typical polymeric MDI consists of approximately 35-50% of pure MDI, 25-35% of triisocyanate (oligomer of the above formula with n=1), 10-20% of tetraisocyanate (n=2), 5-15% of pentaisocyanate (n=3) and 5-10% of higher homologues (n≥4); for example ca. 40% of pure MDI, ca. 30% of triisocyanate (oligomer of the above formula with n=1), ca. 15% of tetraisocyanate (n=2), ca. 10% of pentaisocyanate (n=3) and ca. 5% of higher homologues (n≥4); "ca." indicating a possible deviation of ±20%. The average NCO functionality of a standard polymeric MDI is about 2.7 with a typical viscosity (determined according to DIN 53018) of approximately 200-220 mPa·s at 25° C. Typically the average NCO content is 31-32% by weight. "Pure MDI" consists mainly of 2,4'-MDI and 4,4'-MDI. Again, the term "about" includes determination errors of the functionality.

Thus, in a preferred embodiment, the shell of the microcapsules of the invention comprises a polyaddition product of polymeric methylene diphenyl diisocyanate (polymeric MDI; PMDI) having an average NCO functionality in the range of 2.0 to 4.0, preferably 2.1 to 3.2, in particular 2.3 to 3.0, specifically 2.5 to 2.9, very specifically about 2.7, and at least one amine having at least two primary amino groups.

Such PMDIs are commercially available, for example from BASF SE under the tradenames Lupranat® M10, e.g. Lupranat® M10 R, Lupranat® M20, e.g. Lupranat® M20 R, Lupranat® M20 S or Lupranat® M20 FB; Lupranat® M50; or Lupranat® M70 R. Specifically, a Lupranat® M20, and very specifically Lupranat® M20 S is used.

Apart from the mandatory diphenylmethane diisocyanate and/or oligomers thereof, the shell may also be based on other polyisocyanates.

Suitable other polyisocyanates are known, e.g., from U.S. 2010/0248963 A1, paragraphs [0135] to [0158]. Suitable polyamines are known, e.g. from U.S. 2010/0248963 A1, paragraphs [0159] to [0169].

Suitable other polyisocyanates are for example aliphatic isocyanates or aromatic isocyanates different from diphenylmethane diisocyanate and its oligomers. These isocyanates may be present as monomeric or oligomeric isocyanates. The NCO content may be determined according to ASTM D 5155-96 A.

The term "aliphatic isocyanates" as used herein also includes cycloaliphatic isocyanates. Examples of suitable aliphatic diisocyanates include tetramethylene diisocyanate, pentamethylene diisocyanate, hexamethylene diisocyanate (HMDI), dodecyl diisocyanate, 1,4-diisocyanato-4-methylpentane, 2-butyl-2-ethylpentamethylene diisocyanate, 2,2,4- or 2,4,4-trimethyl-1,6-hexamethylene diisocyanate, lysine alkyl ester diisocyanate, where alkyl stands for $C_1$-$C_{10}$-alkyl, as well as cycloaliphatic isocyanates such as isophoronediisocyanate (IPDI), 1,4-bisisocyanatocyclohexane, bis-(4-isocyanatocyclohexyl)methane, 2-isocyanatopropylcyclohexyl isocyanate, 3(4)-isocyanatomethyl-1-methylcyclohexyl isocyanate, 2,4'-methylenebis(cyclohexyl) diisocyanate, and 4-methylcyclohexane 1,3-diisocyanate (H-TDI). One example of aliphatic triisocyanates is 4-isocyanatomethyl-1,8-octamethylene diisocyanate.

The term "aromatic isocyanates" as used herein also includes araliphatic isocyanates in which at least one of the isocyanate groups is not bound to the aromatic ring, but to an alkyl group bound in turn to the aromatic ring. Suitable aromatic isocyanates include toluene diisocyanates (TDI), such as 2,4-toluene diisocyanate (2,4-TDI) or 2,6-toluene diisocyanate (2,6-TDI) or mixtures thereof (TDI: a mixture of the 2,4- and 2,6-isomers), triisocyanatotoluene, 4,4',4"-triphenylmethane triisocyanate, 2,4,4'-diphenyl ether triisocyanate, 3,3'-dimethyl-4,4'-diphenyl diisocyanate, 3,3'-dimethoxy-4,4'-diphenyl diisocyanate, 1,3- and 1,4-phenylene diisocyanate, diphenyl diisocyanate, 1,5-naphthylene diisocyanate, xylylene diisocyanate or tetramethylxylylene diisocyanate.

Also suitable are oligoisocyanates or polyisocyanates which can be prepared from the abovementioned di- or polyisocyanates or mixtures thereof by means of linking via urethane, allophanate, urea, biuret, uretdione, amide, isocyanurate, carbodiimide, uretonimine, oxadiazinetrione or iminooxadiazinedione structures. Examples are the tetramethylene diisocyanate trimer (i.e. the respective isocyanurate), hexamethylene diisocyanate trimer (i.e. the respective isocyanurate), isophorone diisocyanate trimer (i.e. the respective isocyanurate), and the like. The oligomeric or polymeric isocyanates have an average NCO functionality which is generally in the range of 2.0 to 4.0, preferably 2.1 to 3.2, and more preferably 2.3 to 3.0. Typically, these oligomeric isocyanates have a viscosity (determined according to DIN 53018: 25° C.) in the range from 20 to 1000 mPas, more preferably from 80 to 500 mPas and especially from 150 to 320 mPas. Such oligomeric isocyanates are commercially available, for example from BASF SE under the tradename Basonat® A270.

It is also possible to use masked (blocked) di- or polyisocyanates. In masked or blocked di- or polyisocyanates the isocyanate groups are reacted reversibly to form another functional group that under appropriate conditions can be converted back into the isocyanate group. Preferably the isocyanate group is reacted with an alcohol, preferably a monoalcohol, to form a urethane group. The alcohol is generally eliminated simply during the reaction of the blocked di- or polyisocyanate with the polyamine. Blocking the isocyanate groups lowers the very high reactivity of the isocyanates and enables controlled reaction with the polyamine and hence controlled construction of polyureas.

Also suitable are adducts of diisocyanates with polyhydric alcohols, such as ethylene glycol, glycerol and trimethylolpropane, obtained by addition, per mole of polyhydric alcohol, of a number of moles of diisocyanate corresponding to the number of hydroxyl groups of the respective alcohol and mixtures thereof with the aforementioned diisocyanates. In this way, several molecules of diisocyanate are linked through urethane groups to the polyhydric alcohol to form high molecular weight polyisocyanates. A particularly suitable product of this kind, DESMODUR® L (Bayer Corp., Pittsburgh), can be prepared by reacting three moles of toluene diisocyanate with one mole of 2-ethylglycerol (1,1-bismethylolpropane). Further suitable products are obtained by addition of hexamethylene diisocyanate or isophorone diisocyanate with ethylene glycol or glycerol.

Of the above other polyisocyanates, preference is given to HMDI, HMDI oligomers, especially HMDI-isocyanurat, IPDI, IPDI oligomers, especially IPDI-isocyanurat, xylylene diisocyanate and tetramethylxylylene diisocyanates.

If such further polyisocyanates are used, their overall amount generally makes up at most 20% by weight, preferably at most 10% by weight, in particular at most 5% by weight of the total weight of the polyisocyanates used for forming the shell. Otherwise expressed, if such further polyisocyanates are used, the mandatory diphenylmethane diisocyanate and/or oligomers thereof generally make up at least 80% by weight, preferably at least 90% by weight, in particular at least 95% by weight of the total weight of the polyisocyanates used for forming the shell.

In a particular embodiment, however, no polyisocyanate other than the mandatory diphenylmethane diisocyanate and/or oligomers thereof is used.

Suitable amines having at least two primary amino groups are compounds that contain two and more primary amino groups in the molecule, which amino groups may be linked to aliphatic or aromatic moieties. If the amino groups are linked to aliphatic moieties, the amines are also termed "aliphatic polyamines". They are termed "aliphatic diamines" if only two primary amino groups and no further (primary, secondary or tertiary) amino groups are present. If the amino groups are linked to aromatic moieties, the amines are also termed "aromatic polyamines". They are termed "aromatic diamines" if only two primary amino groups and no further (primary, secondary or tertiary) amino groups are present.

The term "aliphatic polyamines" as used herein includes cycloaliphatic amines. Examples of suitable aliphatic polyamines are α,ω-diamines of the formula $H_2N$—$(CH_2)_p$—$NH_2$, wherein p is an integer from 2 to 8. Exemplary of such diamines are ethylene diamine, propylene-1,3-diamine, tetramethylene diamine, pentamethylene diamine, hexamethylene diamine, heptamethylene diamine and octametylene diamine. Preferably, n is 2 to 6, in particular 4, 5 or 6 and specifically 6; and thus a specific diamine is hexamethylene diamine. Further suitable aliphatic polyamines are polyethylenimines of the formula $H_2N$—$(CH_2$—$CH_2$—$NH)_q$—H, wherein q is an integer from 2 to 20, preferably 3 to 5. Representative examples of such polyethylenimines are diethylene triamine, triethylene tetramine, tetraethylene pentamine and pentaethylene hexamine. Further suitable aliphatic polyamines are dioxaalkane-α,ω-diamines, such as 4,9-dioxadodecane-1,12-diamine of the formula $H_2N$—$(CH_2)_3O$—$(CH_2)_4O$—$(CH_2)_3$—$NH_2$. Further suitable aliphatic polyamines are amines carrying 3 aminoalkyl groups. Examples are tris(2-aminoethyl)amine, tris(2-aminopropyl)amine, tris(3-aminopropyl)amine, tris(2-aminobutyl)amine, tris(3-aminobutyl)

amine, tris(4-aminobutyl)amine, tris(5-aminopentyl)amine and tris(6-aminohexyl)amine. Further suitable aliphatic polyamines are cycloaliphatic diamines, such as isophorone diamine, diaminodicyclohexylmethane or bis(aminomethyl)cyclohexane.

Examples of suitable aromatic polyamines are 1,3-phenylene diamine, 2,4- and 2,6-toluene diamine, 4,4'-diaminodiphenyl methane, 1,5-diaminonaphthalene, 1,3,5-triaminobenzene, 2,4,6-triaminotoluene, 1,3,6-triaminonaphthalene, 2,4,4'-triaminodiphenyl ether, 3,4,5-triamino-1,2,4-triazole and 1,4,5,8-tetraaminoanthraquinone.

Those polyamines which are insoluble or insufficiently soluble in water may be used as their hydrochloride salts.

The polyamines may be used individually or as mixtures of two or more polyamines.

Preferred amines are aliphatic diamines, in particular the above-mentioned α,ω-diamines, i.e. aliphatic diamines of the formula $H_2N—(CH_2)_p—NH_2$, wherein p is an integer from 2 to 8, preferably 2 to 6, in particular 4, 5 or 6. Specifically, hexamethylene diamine is used. Hexamethylene diamine can also be used in admixture with one or more other amines having at least two primary amino groups, in particular with one or more other aliphatic diamines, such as those mentioned above. If hexamethylene diamine is used in such an admixture, it generally makes up at least least 80% by weight, preferably at least 90% by weight, in particular at least 95% by weight of the total weight of the amines used for forming the shell.

The relative amount of each complementary wall-forming component will vary with their equivalent weights. In general, approximately stoichiometric amounts (of isocyanate-groups to primary amino groups) are preferred, while an excess of one component may also be employed, especially an excess of polyisocyanate (to be more precise an excess of isocyanate groups, including masked isocyanate groups and precursors of isocyanate groups which can react with the amino groups to urea groups, such as in isocyanurates, to primary amino groups). The total amount of wall-forming components approximately corresponds to the total amount of polymeric wall-forming materials.

The polyaddition product of the shell is preferably selected from polyureas prepared from
at least one oligomer of formula

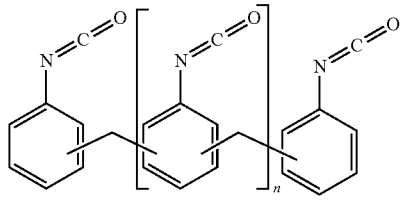

wherein n is at least 1, preferably from 1 to 10, where the oligomer is optionally used in admixture with diphenylmethane diisocyanate, optionally preferably in admixture with diphenylmethane-4,4'-diisocyanate, diphenylmethane-2,4'-diisocyanate and/or diphenylmethane-2,2'-diisocyanate; in particular optionally in admixture with diphenylmethane-4,4'-diisocyanate or with a mixture comprising diphenylmethane-4,4'-diisocyanate and diphenylmethane-2,4'-diisocyanate; and
at least one aliphatic diamine of the formula $H_2N—(CH_2)_p—NH_2$, wherein p is an integer from 2 to 8, preferably 2 to 6, more preferably 4, 5 or 6.

In some instances, in such mixtures of 2,4'-MDI and 4,4'-MDI, diphenylmethane-4,4'-diisocyanate (4,4'-MDI) can be present in an amount of at least 70% by weight, more preferably of at least 80% by weight, in particular of at least 90% by weight, and especially of at least 95% by weight, based on the total weight of this mixture.

The polyaddition product of the shell is specifically selected from polyureas prepared from
polymeric methylene diphenyl diisocyanate (PM DI; see above definition), in particular PMDI having an average NCO functionality in the range of 2.0 to 4.0, preferably 2.1 to 3.2, in particular 2.3 to 3.0, specifically 2.5 to 2.9 and very specifically about 2.7; and
hexamethylene diamine.

The polyaddition product of the shell is very specifically selected from polyureas prepared from
polymeric methylene diphenyl diisocyanate (PMDI; see above definition) having an average NCO functionality in the range of 2.5 to 2.9 and in particular about 2.7; an NCO content of 31-32% by weight and a viscosity of 200 to 220 mPa·s at 25° C. (determined according to DIN 53018); and
hexamethylene diamine.

In a specific embodiment, the microcapsules of the invention have a release profile such that in a standardized release test, 7 days after application, 70 to 95% of the cinmethylin contained in the microcapsules has been released and that simultaneously 24 h after application, 20 to 60% of the cinmethylin contained in the microcapsules has been released.

The standardized release test is as follows:

First a 10% solution of Poloxamer 335 (Pluronic® PE 10500) is prepared which is adjusted to pH 5 with acetic acid. This solution acts as receiver solution for the non encapsulated active compound (here cinmethylin) or, as is presently the case, the released active (here cinmethylin). To 250 ml of the receiver solution 125 mg of the microcapsule suspension is added. The solution is stirred and at defined time points, a sample is drawn. A 0.2 μm Teflon filter is used to remove the remaining microcapsules. In the filtrate, the pesticide is determined via reverse phase HPLC and normalized in a way that the entire amount of the pesticide would account for 100%. This would have been found for example if no encapsulation would have taken place (like in an EC formulation) or all of the pesticide would have been released.

The above ideal release profile ensures a sufficient long-term activity of cinmethylin on the site of application, it impedes or at least reduces significantly its undesired distribution into the environment and it avoids the contamination of the farmer with cinmethylin during application to the soil, plants etc. These ideal release properties are rendered possible by the isocyanate compound used, especially by the use of the above-described oligomers and especially the above-characterized PMDI, and by the weight ratio of cinmethylin to shell, especially by the above preferred ratios.

Another aspect of the present invention is a composition comprising the microcapsules of the invention and a dispersing medium (composition A).

The microcapsules of the invention may be combined with other pesticides, the latter being present outside the microcapsules.

Thus, another aspect of the present invention is a composition (composition B) comprising
(i) the microcapsules of the invention;
(ii) at least one herbicide different from cinmethylin; and
(iii) optionally a dispersing medium.

In composition B, the at least one herbicide different from cinmethylin is not present in the microcapsules.

Preferably, composition B also contains a dispersing medium (iii).

In particular, the compositions of the invention do not contain any vinylpyrrolidone cool terpolymer emulsifiers and especially do not contain the vinylpyrrolidone co- or terpolymer emulsifiers used in WO 94/213139.

Unless specified otherwise, the below remarks refer both to compositions A and B.

Dispersing media are preferably liquid media in which the microcapsules are dispersed and form, e.g., a suspension. Preferably, the liquid dispersing medium is water The composition of the invention is preferably a liquid composition at 20° C. Thus, preferably, the dispersing medium is preferably a liquid medium in which the microcapsules are dispersed. Preferably, the liquid dispersing medium is water. Thus, more preferably, the composition is an aqueous dispersion. In the aqueous dispersion water or an aqueous medium is usually the continuous phase, while the microcapsules form the disperse phase.

The "aqueous medium" comprises an aqueous solvent and optionally compounds dissolved therein, e.g. surfactants as mentioned below or other conventional formulation additives, such as thickeners or biocides; see also below. The aqueous solvent in the aqueous medium is either water or a mixture of water with a water-miscible organic solvent, such as $C_1$-$C_4$-alkanols, e.g. methanol, ethanol, n-propanol, isopropanol, n-butanol, 2-butanol, isobutanol, or tert-butanol, $C_2$-$C_5$-alkanediols and $C_3$-$C_8$-alkanetriols, which are preferably selected from the group consisting of ethylene glycol, 1,2-propanediol, 1,3-propanediol, glycerol and 1,4-butanediol. If the aqueous solvent is a mixture of water and the aforementioned water-miscible organic solvent, the weight ratio of water to water-miscible organic solvent in the aqueous solvent is preferably in the range of from 99:1 to 1:1; more preferably in the range of from 50:1 to 3:1; and most preferably in the range of from 20:1 to 4:1. Expressed differently, the amount of organic solvent may be from 1 to 50% by weight, more preferably from 2 to 25% by weight, and most preferably from 5 to 20% by weight, based on the total weight of the aqueous solvent. In a particular embodiment, the aqueous solvent consists essentially of water, which means that water makes up for at least 96% by weight, preferably at least 98% by weight of the aqueous solvent.

The aqueous dispersion comprises preferably at least 15% by weight, more preferably at least 25% by weight, and in particular at least 35% by weight of water, based on the total weight of the dispersion.

In particular, the composition of the invention is a capsule suspension.

The composition of the invention contains the microcapsules in an amount of preferably from 10 to 70% by weight, more preferably from 20 to 60% by weight, even more preferably from 30 to 50% by weight, in particular from 35 to 50% by weight, based on the total weight of the composition.

The composition of the invention contains cinmethylin in an amount of preferably from 10 to 70% by weight, more preferably from 20 to 60% by weight, even more preferably from 30 to 50% by weight, in particular from 35 to 45% by weight and specifically from 40 to 45% by weight, based on the total weight of the composition.

The composition of the invention may comprise at least one further auxiliary. Suitable auxiliaries are for example: surfactants, further dispersants, e.g. inorganic dispersants, emulsifiers, wetting agents, further adjuvants, (water-soluble) inorganic salts, solubilizers, penetration enhancers, protective colloids, adhesion agents, thickeners, humectants, antifoams, antifreeze agents, stabilizers, antimicrobial agents, pigments, colorants, buffers. Among these, preference is given to surfactants, further dispersants, wetting agents, thickeners, antifoams, antifreeze agents, antimicrobial agents and buffers.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

The composition may comprise a sulfonate dispersant selected from lignosulfonate, naphthalene sulfonate formaldehyde condensate, or mixtures thereof. Preferably, the sulfonate dispersant is selected from lignosulfonate or mixtures of lignosulfonate and naphthalene sulfonate formaldehyde condensate. In particular, the sulfonate dispersant is lignosulfonate.

Lignosulfonates are known and are defined, for example, in Roempp's dictionary of chemistry, 9th Edition, volume 3, Georg-Thieme Verlag, Stuttgart, New York 1990, page 2511. Lignosulfonates which are suitable are the alkali metal salts and/or alkaline earth metal salts and/or ammonium salts, for example the ammonium, sodium, potassium, calcium or magnesium salts of lignosulfonic acid. The sodium, potassium and/or calcium salts are preferably used. Naturally, the term lignosulfonates also encompasses mixed salts of different ions, such as potassium/sodium lignosulfonate, potassium/calcium lignosulfonate and the like, in particular sodium/calcium lignosulfonate. The molecular mass of the lignosulfonate may vary from 500 to 200,000 Da. Preferably, the lignosulfonate has a molecular weight of 700 to 50,000 Da, more preferably from 900 to 20,000 Da, and in particular from 1000 to 10,000 Da, specifically from 1000 to 5000 Da. The lignosulfonate is usually soluble in water (e.g. at 20° C.), e.g. at least 5% by weight, preferably at least 10% by weight, and in particular at least 20% by weight.

In one aspect the lignosulfonate is based on kraft lignins. Kraft lignins are obtained in a pulping process of lignins with sodium hydroxide and sodium sulfide. The kraft lignins are sulfonated to obtain the lignosulfonate.

Naphthalene sulfonate formaldehyde condensates are oligomers obtainable by reaction (e.g. polycondensation) of naphthalene sulfonate and formaldehyde. The naphthalene sulfonate formaldehyde condensate has usually a molecular mass of 300 to 10,000 Da, preferably of 500 to 5000 Da, and in particular of 500 to 2500 Da. The naphthalene group may optionally substituted by a linear or branched $C_1$-$C_8$ alkyl. The naphthalene sulfonate formaldehyde condensates is usually soluble in water (e.g. at 20° C.), e.g. at least 5% by weight, preferably at least 10% by weight, and in particular at least 20% by weight. Naphthalene sulfonate formaldehyde condensates which are suitable are the alkali metal salts and/or alkaline earth metal salts and/or ammonium salts, for example the ammonium, sodium, potassium, calcium or magnesium salts of lignosulfonic acid. The sodium, potassium or calcium salts are preferably used, the sodium, potassium and/or calcium salts are very particularly preferably used.

The composition may comprise from 0.05 to 15% by weight, preferably from 0.1 to 5% by weight, more preferably from 0.3 to 3% by weight and in particular from 0.5 to 2.0% by weight of the sulfonate dispersant (e.g. the lignosulfonate and/or the naphthalene sulfonate formaldehyde condensates).

Suitable nonionic surfactants are alkoxylate surfactants, N-substituted fatty acid amides, amine oxides, esters, sugar-based surfactants, polymeric surfactants, and mixtures thereof. Examples of alkoxylate surfactants are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are homo- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable further adjuvants are compounds which have a neglectable or even no herbicidal activity themselves, and which improve the biological performance of the herbicides on the target. Examples are surfactants, mineral or vegetable oils, and other auxilaries. Further examples are listed by Knowles. Adjuvants and additives, Agrow Reports D5256, T&F Informa UK, 2006, chapter 5.

Further dispersants are for example inorganic dispersants. Suitable inorganic dispersants, also termed anticaking agents, are useful for preventing agglutination of the microcapsules, and are for example silica (such as, for example Sipernat® 22 from Degussa), alumina, calcium carbonate and the like, among which silica is preferred. The concentration of inorganic dispersants in the composition of the invention will generally not exceed 2% by weight, based on the total weight of the final suspension, and, if present, it is preferably in the range from 0.01 to 2% by weight, in particular from 0.02 to 1.5% by weight and especially from 0.1 to 1% by weight, based on the total weight of the composition.

Suitable inorganic salts are water-soluble and are for example selected from sulfates, chlorides, nitrates, mono and dihydrogen phosphates of alkali metals, the sulfates, chlorides, nitrates, mono and dihydrogen phosphates of ammonia, chlorides and nitrates of alkaline earth metals and magnesium sulfate. Examples include lithium chloride, sodium chloride, potassium chloride, lithium nitrate, sodium nitrate, potassium nitrate, lithium sulfate, sodium sulfate, potassium sulfate, sodium monohydrogen phosphate, potassium monohydrogen phosphate, sodium dihydrogen phosphate, potassium dihydrogen phosphate, magnesium chloride, calcium chloride, magnesium nitrate, calcium nitrate, magnesium sulfate, ammonium chloride, ammonium sulfate, ammonium monohydrogen phosphate, ammonium dihydrogen phosphate and the like. Preferred inorganic salts are sodium chloride, potassium chloride, calcium chloride, ammonium sulfate and magnesium sulfate with ammonium sulfate and magnesium sulfate being especially preferred.

The composition may contain the water-soluble inorganic salt in an amount of from 1 to 200 g/L, preferably from 2 to 150 g/L and especially from 10 to 130 g/L. Water-solubility of the salt means solubility in water of at least 50 g/L, in particular at least 100 g/L or even at least 200 g/L at 20° C.

In another embodiment, the composition does not contain or contains less than 10 g/L, in particular less than 1 g/L of the water-soluble inorganic salt.

Protective colloids are for example polyvinylalcohols, starch, cellulose derivatives or copolymers containing vinylpyrrolidone.

Suitable thickeners are compounds which affect the flow behavior of composition of the invention, especially if this is an aqueous dispersion, e.g. a suspension concentrate or a capsule concentrate, and may assist in stabilizing the aqueous suspension of the microcapsules against caking. Mention may be made, in this connection, for example, of commercial thickeners based on polysaccharides, such as methylcellulose, carboxymethylcellulose, hydroxypropylcellulose (Klucel® grades), Xanthan Gum (commercially available e.g. as Kelzan® grades from Kelco or Rhodopol® grades from Rhodia), synthetic polymers, such as acrylic acid polymers (Carbopol® grades), polyvinyl alcohol (e.g. Mowiol® and Poval® grades from Kuraray), polyvinyl pyrrolones, polycarboxylates, polyethers or isocyanate-linked polyethers, silicic acid or phyllosilicates, such as montmorillonite and bentonites, which may be hydrophobized, (commercially available as Attaclay® grades and Attaflow® grades from BASF SE; or as Veegum® grades and Van Gel® grades from R.T. Vanderbilt). In the context of the present invention, Xanthan Gum is a preferred thickener. The concentration of thickeners in the aqueous suspension will generally not exceed 2% by weight, based on the total weight of the aqueous suspension, and is preferably in the range from 0.01 to 2% by weight, in particular from 0.02 to 1.5% by weight and especially from 0.1 to 1% by weight, based on the total weight of the aqueous suspension or the final formulation, respectively.

Suitable antimicrobial agents (preservatives) to prevent microbial spoiling of the compositions of the invention include formaldehyde, alkyl esters of p-hydroxybenzoic acid, sodium benzoate, 2-bromo-2-nitropropane-1,3-diol (bronopol), o-phenylphenol, isothiazolinones, such as benzisothiazolinone or alkylisothiazolinones, e.g. 5-chloro-2-methyl-4-isothiazolinone, pentachlorophenol, 2,4-dichlorobenzyl alcohol and mixtures thereof. Commercially available preservatives that are based on isothiazolinones are for example marketed under the trademarks Proxel® (Arch Chemical), Acticide® MBS (Thor Chemie) and Kathon® MK (Rohm & Haas).

Suitable anti-freezing agents are ethylene glycol, propylene glycol, urea and glycerin.

Antifoam agents suitable for the compositions according to the invention are, for example, silicones, especially silicone emulsions (such as, for example, Silicone SRE-PFL from Wacker or Rhodorsil® from Bluestar Silicones), polysiloxanes and modified polysiloxanes including polysiloxane blockpolymers such as FoamStar® SI and Foam- Star® ST products of BASF SE, long-chain alcohols, fatty acids, salts of fatty acids, organofluorine compounds and mixtures thereof.

Suitable pigments and colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

If appropriate, the composition according to the invention, in particular if this is an aqueous dispersion, may comprise buffers to regulate the pH. Examples of buffers are alkali metal salts of weak inorganic or organic acids such as, for example, phosphoric acid, boric acid, acetic acid, propionic acid, citric acid, fumaric acid, tartaric acid, oxalic acid and succinic acid.

Suitable tackifiers or binders are polyvinylpyrrolidons, polyvinylacetates, polyvinyl alcohols, polyacrylates, biological or synthetic waxes, and cellulose ethers.

The composition generally comprises the auxiliaries in an overall amount of at most 20% by weight, preferably at most 15% by weight, based on the total weight of the composition.

The at least one further herbicide contained in composition B is preferably selected from the group consisting of:
- (ii.1) herbicides from the group of the lipid biosynthesis inhibitors, which are in turn selected from the group consisting of:
  - ACC-herbicides selected from the group consisting of alloxydim, alloxydimsodium, butroxydim, clethodim, clodinafop, clodinafop-propargyl, cycloxydim, cyhalofop, cyhalofop-butyl, diclofop, diclofop-methyl, fenoxaprop, fenoxapropethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-ylcarbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-ylcarbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-ylcarbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-ylcarbonic acid methyl ester (CAS 1033760-58-5); and
  - non ACC herbicides selected from the group consisting of benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;
- (ii.2) herbicides from the group of the ALS inhibitors, which are in turn selected from the group consisting of:
  - sulfonylureas selected from the group consisting of amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methylsodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron,
  - imidazolinones selected from the group consisting of imazamethabenz, imazamethabenz-methyl, imazamox, imazapic, imazapyr, imazaquin and imazethapyr, triazolopyrimidine herbicides and sulfonanilides selected from the group consisting of cloransulam, cloransulam-methyl, diclosulam, flumetsulam, florasulam, metosulam, penoxsulam, pyrimisulfan and pyroxsulam,
  - pyrimidinylbenzoates selected from the group consisting of bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), and N-(4-bromophenyl)-2-[(4,6-dimethoxy-2-pyrimidinyl)oxy]benzenemethanamine (CAS 420138-01-8), sulfonylaminocarbonyl-triazolinone herbicides selected from the group consisting of flucarbazone, flucarbazone-sodium, propoxycarbazone, propoxycarbazonesodium, thiencarbazone and thiencarbazone-methyl; and triafamone;
- (ii.3) herbicides from the group of the photosynthesis inhibitors, which are in turn selected from the group consisting of:
  - amicarbazone,
  - inhibitors of the photosystem II selected from the group consisting of triazine herbicides, in turn selected from the group consisting of chlorotriazine, triazinones, triazindiones, methylthiotriazines and pyridazinones in turn selected from the group consisting of ametryn, atrazine, chloridazone, cyanazine, desmetryn, dimethametryn, hexazinone, metribuzin, prometon, prometryn, propazine, simazine, simetryn, terbumeton, terbuthylazin, terbutryn and trietazin, aryl urea herbicides selected from the group consisting of chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates selected from the group consisting of desmedipham, karbutilat, phenmedipham and phenmedipham-ethyl, nitrile herbicides selected from the group consisting of bromofenoxim, bromoxynil and its salts and esters, and ioxynil and its salts and esters, uraciles selected from the group consisting of bromacil, lenacil and terbacil, bentazon and bentazon-sodium, pyridate, pyridafol, pentanochlor, propanil and inhibitors of the photosystem I selected from the group consisting of diquat, diquat-dibromide, paraquat, paraquat-dichloride and paraquat-dimetilsulfate;

(ii.4) herbicides from the group of the protoporphyrinogen-IX oxidase inhibitors, which are in turn selected from the group consisting of:

acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate (CAS 948893-00-3), and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-02-4);

(ii.5) herbicides from the group of the bleacher herbicides, which are in turn selected from the group consisting of:

PDS inhibitors selected from the group consisting of beflubutamid, diflufenican, fluridone, flurochloridone, flurtamone, norflurazon, picolinafen, and 4-(3-trifluoromethyl phenoxy)-2-(4-trifluoromethylphenyl)pyrimidine (CAS 180608-33-7), HPPD inhibitors selected from the group consisting of benzobicyclon, benzofenap, bicyclopyrone, clomazone, fenquinotrione, isoxaflutole, mesotrione, oxotrione (CAS 1486617-21-3), pyrasulfotole, pyrazolynate, pyrazoxyfen, sulcotrione, tefuryltrione, tembotrione, tolpyralate and topramezone;

aclonifen, amitrole flumeturon and 2-chloro-3-methylsulfanyl-N-(1-methyltetrazol-5-yl)-4-(trifluoromethyl)benzamide;

(ii.6) herbicides from the group of the EPSP synthase inhibitors, which are in turn selected from the group consisting of:

glyphosate, glyphosate-isopropylammonium, glyposate-potassium and glyphosate-trimesium (sulfosate);

(ii.7) herbicides from the group of the glutamine synthase inhibitors, which are in turn selected from the group consisting of:

bilanaphos (bialaphos), bilanaphos-sodium, glufosinate, glufosinate-P and glufosinate-ammonium;

(ii.8) the DHP synthase inhibitor herbicide asulam;

(ii.9) herbicides from the group of the mitosis inhibitors, which are in turn selected from the group consisting of:

compounds of group K1 selected from the group consisting of dinitroanilines in turn selected from the group consisting of benfluralin, butralin, dinitramine, ethalfluralin, fluchloralin, oryzalin, pendimethalin, prodiamine and trifluralin, phosphoramidates selected from the group consisting of amiprophos, amiprophos-methyl, and butamiphos, benzoic acid herbicides selected from the group consisting of chlorthal and chlorthal-dimethyl, pyridines selected from the group consisting of dithiopyr and thiazopyr, benzamides selected from the group consisting of propyzamide and tebutam; compounds of group K2 selected from the group consisting of carbetamide, chlorpropham, flamprop, flamprop-isopropyl, flamprop-methyl, flamprop-M-isopropyl, flamprop-M-methyl and propham;

(ii.10) herbicides from the group of the VLCFA inhibitors, which are in turn selected from the group consisting of:

chloroacetamides selected from the group consisting of acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides selected from the group consisting of flufenacet and mefenacet, acetanilides selected from the group consisting of diphenamid, naproanilide, napropamide and napropamide-M, the tetrazolinone herbicide fentrazamide; and other herbicides selected from the group consisting of anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9

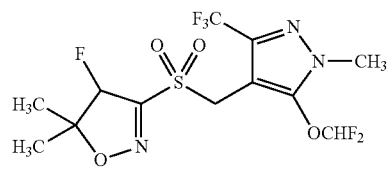

II.1

-continued

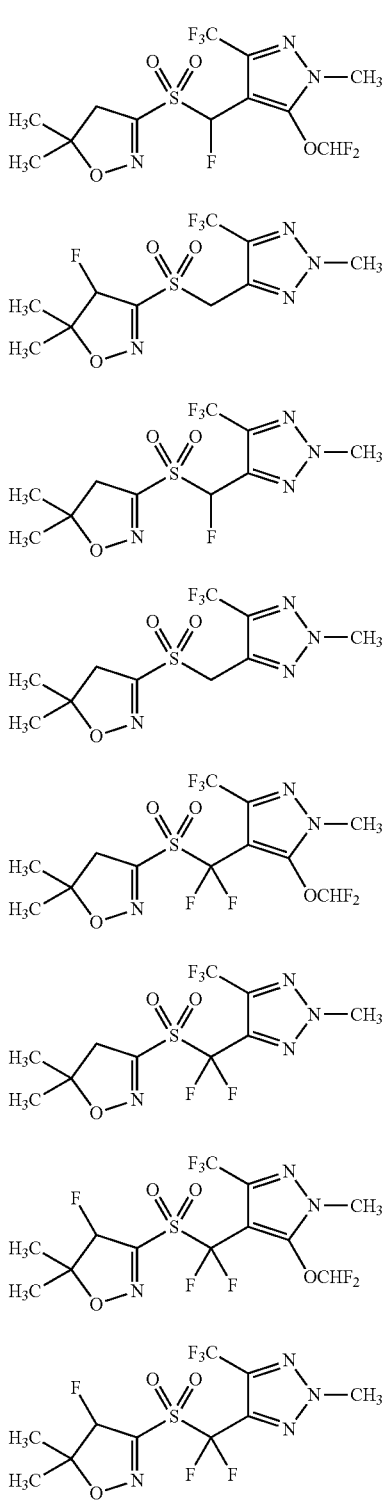

(ii.11) herbicides from the group of the cellulose biosynthesis inhibitors, which are in turn selected from the group consisting of:
chlorthiamid, dichlobenil, flupoxam, indaziflam, isoxaben, triaziflam and 1-cyclohexyl-5-pentafluorphenyloxy-1⁴-[1,2,4,6]thiatriazin-3-ylamine (CAS 175899-01-1);

(ii.12) herbicides from the group of the decoupler herbicides, which are in turn selected from the group consisting of:
dinoseb, dinoterb and DNOC and its salts;

(ii.13) herbicides from the group of the auxinic herbicides, which are in turn selected from the group consisting of:
2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, flopyrauxifen, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, 4-amino-3-chloro-6-(4-chloro-2-fluoro-3-methoxyphenyl)-5-fluoropyridine-2-carboxylic acid, benzyl 4-amino-3-chloro-6-(4-chloro-2-fluoro-3-methoxyphenyl)-5-fluoropyridine-2-carboxylate (CAS 1390661-72-9) and 4-amino-3-chloro-5-fluoro-6-(7-fluoro-1H-indol-6-yl)picolinic acid;

(ii.14) herbicides from the group of the auxin transport inhibitors, which are in turn selected from the group consisting of:
diflufenzopyr, diflufenzopyr-sodium, naptalam and naptalam-sodium; and (ii.15) other herbicides selected from the group consisting of:
bromobutide, chlorflurenol, chlorflurenol-methyl, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flurenol, flurenol-butyl, flurprimidol, fosamine, fosamine-ammonium, indanofan, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine and tridiphane.

More preferably, the at least one herbicide different from cinmethylin is selected from the group consisting of quinmerac, picolinafen, dimethenamid, dimethenamid-P, imazamox, diflufenican, flufenacet, pendimethalin, pyroxasulfone, sulfonylureas selected from the group consisting of amidosulfuron, azimsulfuron, bensulfuron, bensulfuronmethyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, and aminopyralid and its salts.

Even more preferably, the at least one herbicide different from cinmethylin is selected from the group consisting of quinmerac, picolinafen, dimethenamid, dimethenamid-P, diflufenican, flufenacet and pendimethalin, and in particular from the group consisting of quinmerac, picolinafen, diflufenican and flufenacet. Specifically, the at least one herbicide different from cinmethylin is selected from the group consisting of quinmerac and picolinafen.

In the terms of the present invention the composition B is not restricted to a physical mixture (co-formulation) containing the microcapsules and the at least one herbicide different from cinmethylin, but refers to any preparation form of the microcapsules and the at least one herbicide different from cinmethylin, the use of which is time- and locus-related. In one embodiment of the invention, composition B is a physical mixture of the microcapsules and the at least one herbicide different from cinmethylin. In another embodiment of the invention, composition B refers to the microcapsules and the at least one herbicide different from cinmethylin being formulated separately, but in such a form that they can be applied to the soil in which undesired vegetation is growing and/or undesired vegetation and/or cultivated plants to be protected from undesired vegetation and/or on their environment in a temporal relationship, i.e. simultaneously or subsequently, the subsequent application having a time interval which allows a combined action of the two components.

One example for a composition B wherein the microcapsules and the at least one herbicide different from cinmethylin are formulated separately is a combipack. In a combipack, two or more components of the combipack are packaged separately, i.e., not jointly pre-formulated. As such, combipacks include one or more separate containers such as vials, cans, bottles, pouches, bags or canisters, each container containing a separate component for an agrochemical composition. One example is a two-component combipack (two-component-kit).

"Time-related" means that the time interval between the separate application of the two or more herbicides (cinmethylin and the at least one other herbicide) is such that the active compound applied first is still present on the locus of application when the second is applied. This time interval is generally from a few seconds to a few days, e.g. from 1 s to 7 days or from 1 s to 24 h or from 1 s to 12 h.

Preferably however, the composition B is a physical mixture (co-formulation) containing both the microcapsules and the at least one herbicide different from cinmethylin.

In composition B, cinmethylin and the at least one herbicide different therefrom are present in an overall weight ratio of preferably from 100:1 to 1:100, in particular from 50:1 to 1:50, and specifically from 10:1 to 1:10. "Overall" means that the weight ratio refers to the weight of all herbicides different from cinmethylin, should more than one be used.

In addition to the advantages confined by the microcapsules of the invention, composition B has moreover the advantage of allowing the co-formulation of cinmethylin with herbicides which are not compatible therewith in a liquid composition. Incompatibility of two or more pesticides may become manifest, for example, in sediment formation, agglomeration, crystallization and/or syneresis (deposition of liquid formulation constituents). In other cases, the phytotoxicity on cultivated plants may be enhanced by the combination of two or more active compounds in a liquid formulation. Also the combination of cinmethylin with various other herbicides may have major drawbacks. For instance, combining cinmethylin with quinmerac in a suspoemulsion (cinmethylin is an oily liquid and thus generally provided as an emulsion concentrate (EC), while quinmerac is a water-insoluble solid and thus typically formulated as a suspension concentrate (SC), a natural combination of the two formulations thus being a suspoemulsion) leads to strong crystal growth of the quinmerac particles and Ostwald ripening after storage. The problem with Ostwald ripening also occurs when cinmethylin is combined with flufenacet or diflufenican in a suspoemulsion or in an emulsion concentrate. Combining cinmethylin with picolinafen in an emulsion concentrate (both active compounds are typically formulated as EC) leads to a severe increase of the phytotoxicity on cultivated plants. These problems are solved by composition B of the invention.

In another aspect, the present invention relates to a method for preparing the microcapsules of the invention or the composition of the invention, comprising polymerizing diphenylmethane diisocyanate and/or at least one oligomer thereof and at least one amine having at least two primary amino groups in the presence of cinmethylin, where cinmethylin and the diphenylmethane diisocyanate and/or at least one oligomer thereof are used in an overall weight ratio of from 50:1 to 150:1, preferably from 60:1 to 120:1, more preferably from 70:1 to 100:1, in particular from 75:1 to 95:1, specifically from 80:1 to 90:1.

For preparing a composition which is an aqueous dispersion, e.g. a capsule suspension, the reaction of the monomers is expediently carried out in the presence of water.

The microcapsules of the invention or the composition of the invention are preferably prepared by an interfacial polymerization process of the polyurea wall forming material, i.e. the above-defined polyisocyanates and polyamines. Interfacial polymerization is usually performed in an aqueous oil-in-water emulsion or suspension of the core material containing dissolved therein at least one part of the polymer wall forming material. During the polymerization, the polymer segregates from the core material to the boundary surface between the core material and water thereby forming the wall of the microcapsule. Thereby an aqueous suspension of the microcapsule material is obtained.

Polyisocyanates react rather fast with water, yielding carbamic acid, which, due to its instability, decomposes into the corresponding amine and $CO_2$. If this reaction is not desired, and the polyisocyanate is intended to react essentially only with the polyamine, it is expedient to avoid any essential contact of the polyisocyanate with water. For this purpose, expediently, cinmethylin and the polyisocyanate are first mixed. According to the method of the present invention, cinmethylin is used is excess, the weight ratio of cinmethylin to the polyisocyanate being of from 50:1 to 150:1, preferably from 60:1 to 120:1, more preferably from 70:1 to 100:1, in particular from 75:1 to 95:1, specifically from 80:1 to 90:1. In this mixture the polyisocyanate is sufficiently protected from hydrolysis. If desired, the mixture can also contain one or more organic solvents, suitably organic solvents which are not miscible with water. Suitable water-immiscible organic solvents are described above in context with water-immiscible organic solvents optionally contained in the core.

The resulting mixture is then mixed with water and optionally also with one or more of the above-described auxiliaries. Mixing with water generally includes a step of high speed or high sheer mixing to obtain an oil-in-water emulsion, which can be carried out with any high speed or high shear mixer known in the art. Suitable mixing devices include in particular high shear mixers, such as Ultra-Turrax apparatus, static mixers, e.g. systems having mixing nozzles, agitator bead mills, colloid mills, cone mills and other homogenizers. Ultra Turrax have suitably fast rotation speed, such as at least 5000 rpm, preferably at least 7000 rpm and in particular at least 10000 rpm. Expediently, the water phase contains one or more dispersants to allow or ease the formation of an emulsion. Suitable dispersants are the above-defined lignosulfonates, naphthalene sulfonate formaldehyde condensates or condensed phenol sulfonates; especially lignosulfonates and/or naphthalene sulfonate formaldehyde condensates.

The aqueous phase may additionally also comprises a water-soluble inorganic salt as defined above and which is preferably selected from sodium chloride, potassium chloride, calcium chloride, ammonium sulfate and magnesium sulfate; and/or an anti-freeze agent as defined above and which is preferably selected from ethylene and propylene glycol. If the mixture may foam, an anti-foaming agent as defined above, for example a silicone defoamer, may also be added.

The particle size distribution resulting from high-shear stirring is typically characterized by the following parameters: a $D_{50}$ of 0.5 to 20 µm and a $D_{90}$ of 5 to 30 µm, more preferably a $D_{50}$ of 1 to 15 µm and a $D_{90}$ of 5 to 20 µm; most preferably a $D_{50}$ of 2 to 10 µm and a $D_{90}$ of 8 to 15 µm (z-average by means of light scattering).

The above mixing step is preferably followed by admixture with the polyamine (amine having at least two primary amino groups). Preferably the polyamine is added to the aqueous mixture, either as such or dissolved or dispersed in water. The ratio of the at least one amine having at least two primary amino groups and the isocyanate compound is preferably such that the molar ratio of all primary amino groups $NH_2$ contained in the amine and all isocyanate groups or reactive precursors of isocyanate groups (i.e. any free or masked isocyanate group or any group which can give isocyanate groups under the given reaction conditions, such as cyanurate groups and the like) contained in the amount of employed polyisocyanate (i.e. of any diphenylmethane diisocyanates, oligomers thereof or any optional further poylisocyanates) is from 2.5:1 to 1:2.5, preferably from 1.5:1 to 1:1.5, in particular from 1.2:1 to 1:1.2. Specifically the isocyanate compound is used in slight excess, so that preferably 1.05 to 1.5 mol of isocyanate group or reactive precursor of isocyanate groups per mol of $NH_2$ group are present (i.e. the ratio of NCO (precursor) to $NH_2$ is specifically 1.5:1 to 1.05:1.

In the specific case of PMDI and hexamethylene diamine, PMDI and hexamethylene diamine are preferably used in an overall weight ratio of from 2:1 to 5:1, in particular from 2:1 to 3:1.

The reaction temperature can range from 10 to 90° C., in particular from 15 to 80° C., preferably from 20 to 70° C. The optimum reaction temperature is chosen so that a polyurea shell with optimum release properties of cinmethylin is produced. Optimum release properties are described above. The optimum reaction temperature depends on the amount of isocyanate compound used, relative to the amount of cinmethylin, and the reactivity thereof. If the monomers are less reactive, more elevated reaction temperatures are expedient, such as 30 to 90° C. or 50 to 70° C. Also if the amount of isocyanate compound, relative to the amount of cinmethylin, is rather low, elevated reaction temperatures are expedient, such as 30 to 90° C. or 50 to 70° C. in order to ensure a higher degree of crosslinking. The optimum reaction temperature for the respective isocyanate compound and the amount used with respect to cinmethylin can be found out by preliminary tests.

If desired, one or more of the above-described auxiliaries can be added during the reaction or after its completion.

For preparing a composition B, the at least one further herbicide different from cinmethylin is then added. Alternatively, and if desired, one or more of the above-described auxiliaries can be added together with the at least one further herbicide or after its addition.

In a more preferred embodiment, the method of the invention comprises following steps:
(a) providing an aqueous phase containing water, a dispersant and/or a surfactant and optionally at least one further ingredient selected from the group consisting of emulsifier. wetting agent, further adjuvant, inorganic salt, solubilizer, penetration enhancer, protective colloid, adhesion agent, thickener, humectant, antifoam, antifreeze agent, stabilizer, antimicrobial agent, pigment, colorant, buffer, tackifier and binder;
(b) providing an oily phase containing cinmethylin and diphenylmethane diisocyanate and/or at least one oligomer thereof, where the oily phase contains cinmethylin and diphenylmethane diisocyanate and/or the at least one oligomer thereof in an overall weight ratio of from 50:1 to 150:1, preferably from 60:1 to 120:1, more preferably from 70:1 to 100:1, in particular from 75:1 to 95:1, specifically from 80:1 to 90:1;
(c) mixing the aqueous phase of step (a) and the oily phase of step (b);
(d) adding at least one amine having at least two primary amino groups to the mixture obtained in step (c) and optionally heating the reaction either during the addition of the diamine or after the addition of the diamine or both;
(e) optionally adding at least one ingredient selected from the group consisting of emulsifier, wetting agent, further adjuvant, solubilizer, penetration enhancer, protective colloid, adhesion agent, thickener, humectant, antifoam, antifreeze agent, stabilizer, antimicrobial agent, pigment, colorant, buffer, tackifier and binder to the mixture obtained in step (d);
(f) optionally adjusting the pH to the desired value; and
(g) optionally bringing the mixture obtained in step (d), (e) or (f) to the desired concentration.

With respect to suitable and preferred diphenylmethane diisocyanate, oligomers thereof and amines having at least two primary amino groups, the above definitions made in context with the microcapsules of the invention as a matter of course apply here, too. Thus, specifically, polymeric methylene diphenyl diisocyanate having an average NCO functionality in the range of 2.0 to 4.0, preferably 2.1 to 3.2, in particular 2.3 to 3.0, specifically 2.5 to 2.9 is used as diphenylmethane diisocyanate or its oligomer and hexamethylene diamine is used as amine having at least two primary amino groups.

The dispersant used in step (a) is not a vinylpyrrolidone co- or terpolymer emulsifier and is especially not one of the vinylpyrrolidone co- or terpolymer emulsifiers used in WO 94/213139.

Preferably, the dispersant used in step (a) is a sulfonate dispersant selected from the group consisting of lignosulfonate, naphthalene sulfonate formaldehyde condensate and mixtures thereof, and is in particular a mixture of at least one lignosulfonate and at least one naphthalene sulfonate formaldehyde condensate.

The aqueous phase provided in step (a) may additionally also comprises a water-soluble inorganic salt as defined above and which is preferably selected from sodium chloride, potassium chloride, calcium chloride, ammonium sulfate and magnesium sulfate; and/or an anti-freeze agent as defined above and which is preferably selected from ethylene and propylene glycol. If an inorganic salt is used, this is added in such amounts that its concentration in the aqueous phase provided in step (a) is from 2 to 150 g/L, preferably from 10 to 130 g/L and especially from 50 to 130 g/L. If the mixture may foam, an anti-foaming agent as defined above, for example a silicone defoamer, may also be added The oily phase provided in step (b) preferably contains cinmethylin in excess, the overall weight ratio of cinmethylin to the diphenylmethane diisocyanate and/or the least one oligomer thereof being from 50:1 to 150:1, preferably from 60:1 to 120:1, more preferably from 70:1 to 100:1, in particular from 75:1 to 95:1, specifically from 80:1 to 90:1.

Mixing in step (c) preferably includes a step of high speed or high sheer mixing, which can be carried out with any high speed or high shear mixer known in the art. Suitable mixing devices include in particular high shear mixers, such as Ultra-Turrax apparatus, static mixers, e.g. systems having mixing nozzles, agitator bead mills, colloid mills, cone mills and other homogenizers. Ultra Turrax have suitably fast rotation speed, such as at least 5000 rpm, preferably at least 7000 rpm and in particular at least 10000 rpm.

In one embodiment of step (c), the oily phase of step (b) is added to the aqueous phase of step (a).

Mixing step (c) preferably provides an oil-in-water emulsion with a particle size distribution of the oil droplets characterized by the following parameters: a $D_{50}$ of 0.5 to 20 μm and a $D_{90}$ of 5 to 30 μm, more preferably a $D_{50}$ of 1 to 15 μm and a $D_{90}$ of 5 to 20 μm; most preferably a $D_{50}$ of 2 to 10 μm and a $D_{90}$ of 8 to 15 μm (z-average by means of light scattering).

In step (d), the at least one amine having at least two primary amino groups can be added either as such or dissolved or dispersed in water. If dissolved or dispersed in water, the amine is generally used as a 5 to 50% by weight, preferably 15 to 35% by weight aqueous solution/dispersion, based on the weight of the solution/dispersion.

The ratio of the at least one amine having at least two primary amino groups added in step (d) and the isocyanate compound used in step (b) is preferably such that the molar ratio of all primary amino groups $NH_2$ contained in the amine and all isocyanate groups or reactive precursors of isocyanate groups (i.e. any free or masked isocyanate group or any group which can give isocyanate groups under the given reaction conditions, such as cyanurate groups and the like) contained in the amount of employed polyisocyanate (i.e. of any diphenylmethane diisocyanates, oligomers thereof or any optional further poylisocyanates) is from 2.5:1 to 1:2.5, preferably 1.5:1 to 1:1.5, in particular from 1.2:1 to 1:1.2. Specifically the isocyanate compound is used in slight excess, so that preferably 1.05 to 1.5 mol of isocyanate group or reactive precursor of isocyanate groups per mol of $NH_2$ group are present (i.e. the ratio of NCO (precursor) to $NH_2$ is specifically 1.5:1 to 1.05:1.

In the specific case of PMDI and hexamethylene diamine, PMDI and hexamethylene diamine are preferably used in an overall weight ratio of from 2:1 to 5:1, in particular from 2:1 to 3:1.

The reaction temperature (see step (d)) can range from 10 to 90° C., in particular from 15 to 80° C., preferably from 20 to 70° C. The optimum reaction temperature is chosen so that a polyurea shell with optimum release properties of cinmethylin is produced. Optimum release properties are described above. The optimum reaction temperature depends on the amount of isocyanate compound used, relative to the amount of cinmethylin, and the reactivity thereof. If the monomers are less reactive, more elevated reaction temperatures are expedient, such as 30 to 90° C. or 50 to 70° C. Also if the amount of isocyanate compound, relative to the amount of cinmethylin, is rather low, elevated reaction temperatures are expedient, such as 30 to 90° C. or 50 to 70° C. in order to ensure a higher degree of cross-linking. The optimum reaction temperature for the respective isocyanate compound and the amount used with respect to cinmethylin can be found out by preliminary tests.

The reaction in step (d) is generally carried out under stirring, generally with a low shear rate.

Steps (e), (f) and (g) are interchangeable.

If desired, one or more of the above-described auxiliaries can be added during the reaction or after its completion (step (e)).

For preparing a composition B, the above preferred method also contains a step (i) in which the at least one further herbicide different from cinmethylin is added. In this case, steps (e), (f), (g) and (i) are interchangeable.

The resulting reaction mixture is often basic and the pH can, if expedient, be adjusted to pH 6 to 8 by the addition of an acid which is acceptable in herbicide formulations, such as hydrochloric acid, sulfuric acid, acetic acid, citric acid and the like.

Another aspect of the invention relates to a composition obtainable by the method of the invention.

The reaction mixture of the microcapsule formation may either be used as such or may be subjected to a purification step, such as filtration in order to remove possible agglomerates, or the microcapsules can be first isolated and then re-suspended in a desired medium such as water or an aqueous medium. Isolation of the microcapsules can be carried out by known means such as filtration or centrifugation, or the aqueous suspension may be spray-dried, granulated or freeze-dried.

The invention also relates to the use of the microcapsules or the composition of the invention for controlling undesired vegetation, and to a method for controlling undesired vegetation comprising treating the soil in which undesired vegetation is growing and/or undesired vegetation and/or cultivated plants to be protected from undesired vegetation and/or on their environment with the microcapsules or composition of the invention.

The microcapsules and the composition of the present invention are suitable for controlling a large number of undesirable vegetation (harmful plants), including monocotyledonous weeds and dicotyledonous weeds.

In one embodiment, the undesirable vegetation is selected from monocotyledonous weed species. Preferably, the undesirable vegetation is selected from the family Poaceae. More preferably, the undesirable vegetation is selected from the tribes Aveneae, Bromeae, Paniceae and Poeae. In one embodiment, the undesirable vegetation is selected from the tribe Aveneae. In another embodiment, the undesirable vegetation is selected from the tribe Bromeae. In yet another embodiment, the undesirable vegetation is selected from the tribe Paniceae. In still another embodiment, the undesirable vegetation is selected from the tribe Poeae.

In particular, the composition of the present invention may be used for controlling annual weeds such as gramineous weeds (grass weeds) including, but not limited to, the genera *Aegilops* such as *Aegilops cylindrical* (AEGCY, jointed goatgrass); *Agropyron* such as *Agropyron repens*

(AGRRE, common couchgrass); *Alopecurus* such as *Alopecurus myosuroides* (ALOMY, blackgrass) or *Alopecurus aequalis* (ALOAE, foxtail); *Apera* such as *Apera spica-venti* (APESV, silky wind grass); *Avena* such as *Avena fatua* (AVEFA, wild oat) or *Avena sterilis* subsp. *sterilis* (AVEST, sterile oat); *Brachiaria* such as *Brachiaria plantaginea* (BRAPL, Alexander grass) or *Brachiaria decumbens* (BRADC, Surinam grass); *Bromus* such as *Bromus inermis* (BROIN, awnless brome), *Bromus sterilis* (BROST, barren bromegrass), *Bromus tectorum* (BROTE, cheatgrass), *Bromus arvensis* (BROAV, field bromegrass), *Bromus secalinus* (BROSE, rye bromegrass) or *Bromus hordeacus* (BROMO, lopgrass); *Cenchrus* such as *Cenchrus echinatus* (CCHEC, Mossman River grass); *Cynodon* such as *Cynodon dactylon* (CYN DA, bermudagrass); *Digitaria* such as *Digitaria ciliaris* (DIGAD, southern crabgrass), *Digitaria sanguinalis* (DIGSA, hairy crabgrass), *Digitaria insularis* (TRCIN, sourgrass) or *Digitaria ischaemum* (DIGIS, smooth crabgrass); *Echinochloa* such as *Echinochloa colonum* (ECHCO, awnless barnyardgrass), *Echinochloa crus-galli* (ECHCG, common barnyard grass), *Echinochloa crus-pavonis* (ECHCV, Gulf cockspurgrass), *Echinochloa oryzoides* (ECHOR, early barnyardgrass) or *Echinochloa phyllogogon* (ECHPH, late barnyardgrass); *Eleusine* such as *Eleusine indica* (ELEIN, Indian goosegrass); *Eriochloa* species such as *Eriochloa villosa*, *Ischaemum* such as *Ischaemum rugusom* (ISCRU, muraina grass); *Leptochloa* such as *Leptochloa chinensis* (LEFCH, Chinese sprangletop), *Leptochloa fascicularis* (LEFFA, salt-meadow grass), *Leptochloa filiformis* (LEFPC, thread sprangletop), *Leptochloa mucronata* (LEFFI, red sprangletop), *Leptochloa panicoides* (LEFPA, tighthead sprangletop), *Leptochloa scabra* (LEFSC) or *Leptochloa virgata* (LEFVI, tropical sprangletop); *Lolium* such as *Lolium multiflorum* (LOLMU, Italian ryegrass), *Lolium perenne* (LOLPE, English ryegrass) or *Lolium rigidum* (LOLRI, annual rye-grass); *Panicum* such as *Panicum capillare* (PANCA, tumble panicgrass), *Panicum dichotomiflorum* (PANDI, smooth witchgrass), *Panicum laevifolium* (PANLF, sweet panicgrass) or *Panicum miliaceum* (PANMI, common millet); *Phalaris* such as *Phalaris minor* (PHAMI, lesser canary grass), *Phalaris paradoxa* (PHAPA, paradoxagrass), *Phalaris canariensis* (PHACA, canarygrass) or *Phalaris brachystachys* (PHABR, short-spiked canarygrass); *Poa* such as *Poa annua* (POAAN, annual bluegrass), *Poa pratensis* (POAPR, Kentucky bluegrass) or *Poa trivialis* (POATR, rough meadowgrass); *Rottboellia* such as *Rottboellia exaltata* (ROOEX, guinea-fowl grass); *Setaria* such as *Setaria faberi* (SETFA, giant foxtail), *Setaria glauca* (PESGL, pearl millet), *Setaria italic* (SETIT, Italian millet), *Setaria pumila* (SETPU, yellow foxtail), *Setaria verticillata* (SETVE, bristly foxtail) or *Setaria viridis* (SETVI, green foxtail); and *Sorghum* such as *Sorghum halepense* (SORHA, Johnson grass).

The composition of the present invention is also suitable for controlling a large number of dicotyledonous weeds, in particular broadleaf weeds including, but not limited to, *Polygonum* species such as *Polygonum convolvulus* (POLCO, wild buckwheat), *Amaranthus* species such as *Amaranthus albus* (AMAAL, tumble pigweed), *Amaranthus blitoides* (AMABL, mat amaranth), *Amaranthus hybridus* (AMACH, green pigweed), *Amaranthus palmeri* (AMAPA, Palmer amaranth), *Amaranthus powellii* (AMAPO, Powell amaranth), *Amaranthus retroflexus* (AMARE, redroot pigweed), *Amaranthus tuberculatus* (AMATU, rough-fruit amaranth), *Amaranthus rudis* (AMATA, tall amaranth) or *Amaranthus viridis* (AMAVI, slender amaranth), *Chenopodium* species such as *Chenopodium album* (CHEAL, common lambsquarters), *Chenopodium ficifolium* (CHEFI, figleaved goosefoot), *Chenopodium polyspermum* (CHEPO, many-seeded goosefoot) or *Chenopodium hybridum* (CHEHY, maple-leaf goosefoot), *Sida* species such as *Sida spinosa* L. (SIDSP, prickly *Sida*), *Ambrosia* species such as *Ambrosia artemisiifolia* (AMBEL, common ragweed), *Acanthospermum* species, *Anthemis* species such as *Anthemis arvensis* (ANTAR, field chamomile), *Atriplex* species, *Cirsium* species, *Convolvulus* species, *Conyza* species such as *Conyza bonariensis* (ERIBO, hairy horseweed) or *Conyza canadensis* (ERICA, Canada horseweed), *Cassia* species, *Commelina* species, *Datura* species, *Euphorbia* species, *Geranium* species such as *Geranium dissectum* (GERDI, cut-leaf *Geranium*), *Geranium pusillium* (GERPU, smallflower *Geranium*) or *Geranium rotundifolium* (GERRT, round-leaved cranesbill), *Galinsoga* species, *Ipomoea* species such as *Ipomoea hederacea* (IPOHE, morningglory), *Lamium* species, *Malva* species, *Matricaria* species such as *Matricaria chamomilla* (MATCH, wild chamomile), *Matricaria discoidea* (MATMT, pineapple weed) or *Matricaria inodora* (MATIN, false chamomile), *Sysimbrium* species, *Solanum* species, *Xanthium* species, *Veronica* species, *Viola* species, *Stellaria* species such as *Stellaria media* (STEME, common chickweed), *Abutilon theophrasti* (ABUTH, velvet leaf), Hemp *Sesbania* (*Sesbania exaltata* Cory, SEBEX, Colorado river hemp), *Anoda cristata* (ANVCR, cottonweed), *Bidens pilosa* (BIDPI, common blackjack), *Centaurea* species such as *Centaurea cyanus* (CENCY, cornflower), *Galeopsis tetrahit* (GAETE common hemp nettle), *Galium aparine* (GALAP, cleavers or goosegrass), *Galium spurium* (GALSP, false cleavers), *Galium tricornutum* (GALTC, corn cleavers), *Helianthus annuus* (HELAN, common sunflower), *Desmodium tortuosum* (DEDTO, giant beggar weed), *Kochia scoparia* (KCHSC, mock cypress), *Mercurialis annua* (MERAN, annual mercury), *Myosotis arvensis* (MYOAR, field forget-me-not), *Papaver rhoeas* (PAPRH, common poppy), *Raphanus raphanistrum, Salsola kali* (SASKA, prickly glasswort), *Sonchus arvensis* (SONAR, corn sowthistle), *Tagetes minuta* (TAGMI, Mexican marigold), *Richardia brasiliensis* (RCHBR, Brazil pusley), cruciferous weeds such as *Raphanus raphanistrum* (RAPRA, wild radish), *Sinapis alba* (SINAL, white mustard), *Sinapis arvensis* (SINAR, wild mustard), *Thlaspi arvense* (THLAR, fanweed), *Descurainia Sophia* (DESSO, flixweed), *Capsella bursa-pastoris* (CAPBP, shepherd's purse), *Sisymbrium* species such as *Sisymbrium officinale* (SSYOF, hedge mustard) or *Sisymbrium orientale* (SSYOR, oriental mustard), *Brassica kaber* (SINAR, wild mustard).

The compositions of the present invention are also suitable for controlling a large number of annual and perennial sedge weeds including *Cyperus* species such as purple nutsedge (*Cyperus rotundus* L.), yellow nutsedge (*Cyperus esculentus* L.), hime-kugu (*Cyperus brevifolius* H.), sedge weed (*Cyperus microiria* Steud), rice flatsedge (*Cyperus iria* L.), and the like.

Preferably, the use and method of the invention serve for controlling at least one of the following undesired plant species: *Abutilon theophrasti, Alopercurus myosuroides, Amaranthus retroflexus, Ambrosia artemisiifolia, Apera spica-venti, Avena fatua, Bidens pilosa, Brachiaria deflexa, Brachiaria plantaginea, Bromus sterilis, Capsella bursa-pastoris, Chenopodium album, Chenopodium album, Commenline benghalensis, Digitaria sanguinales, Echinocloa crus-galli, Eleusine indica, Eriochloa villosa, Erigeron Canadensis, Galium aparine, Lamium amplexicaule, Lamium purpureum, Lolium rigidum, Matricaria inodora, Panicum dichotomiflorun, Papaver rhoeas, Pharbitis pur-* purea, Poa annua, Polygonum convolvulus, Raphanus raphanistrum Setaria lutescens, Setaria faberi, Setaria verticillata, Setaria viridis, Solanum nigrum, Sorghum halepense, Stellaria media, Veronica persica.

Alopecurus myosuroides, Avena fatua, Bromus sterilis, Galium aparine, Lolium rigidum, Matricaria inodora and/or Papaver rhoeas Specifically, the use and method of the invention serve for controlling at least one of the following undesired plant species: Alopecurus myosuroides, Avena fatua, Bromus sterilis, Galium aparine, Lolium rigidum, Matricaria inodora and/or Papaver rhoeas.

Among the above unwanted plants, Alopecurus myosuroides is particularly difficult to control, especially in cereal and rapeseed cultures. Surprisingly, the microcapsules and the composition of the invention has proved to be very effective against Alopecurus myosuroides. Thus, in particular embodiment, the use and method of the invention serve for controlling Alopecurus myosuroides.

Examples of suitable crop plants which are to be protected from unwanted vegetation are cereals, for example wheat (inclusive spelt, einkorn, emmer, kamut, durum and triticale), rye, barley, oats, maize, millet, Sorghum, teff, fonio, or rice; beet, for example sugar or fodder beet; pome fruit, stone fruit and soft fruit, for example apples, pears, plums, peaches, almonds, cherries, strawberries, raspberries, currants or gooseberries; legumes, for example beans, lentils, peas, lucerne or soybeans; oil crops, for example oilseed rape, mustard, olives, sunflowers, coconut, cacao, castor beans, oil palm, peanuts or soybeans; cucurbits, for example pumpkins/squash, cucumbers or melons; fiber crops, for example cotton, flax, hemp or jute; citrus fruit, for example oranges, lemons, grapefruit or tangerines; vegetable plants, for example spinach, lettuce, asparagus, cabbages, carrots, onions, tomatoes, potatoes, pumpkin/squash or capsicums; plants of the laurel family, for example avocados, cinnamon or camphor; energy crops and industrial feedstock crops, for example maize, soybeans, wheat, oilseed rape, sugar cane or oil palm; maize; tobacco; nuts; coffee; tea; bananas; wine (dessert grapes and grapes for vinification); hops; grass, for example turf; sweetleaf (Stevie rebaudania); rubber plants and forest plants, for example flowers, shrubs, deciduous trees and coniferous trees, and propagation material, for example seeds, and harvested produce of these plants.

Preferably, the crop plants which are to be protected from unwanted vegetation are selected from the group consisting of cereals and rapeseed, in particular from wheat, rye, barley, rice, maize, millet, Sorghum, teff, fonio, oats and rapeseed.

Thus, preferably, the use and method of the invention serve for controlling undesired vegetation in cereal cultures and/or in rapeseed cultures; in particular in wheat, rye, barley, rice, maize, millet, Sorghum, teff, fonio, oats and/or rapeseed cultures.

In a specific embodiment, the invention relates to the use of the microcapsules or the composition of the invention for controlling at least one of the following undesired plant species: Alopecurus myosuroides, Avena fatua, Bromus sterilis, Galium aparine, Lolium rigidum, Matricaria inodora and/or Papaver rhoeas; and in particular for controlling Alopecurus myosuroides. More specifically, the invention relates to the use of the microcapsules or the composition of the invention for controlling at least one of the following undesired plant species: Alopecurus myosuroides, Avena fatua, Bromus sterilis, Galium aparine, Lolium rigidum, Matricaria inodora and/or Papaver rhoeas in cereal and/or rapeseed cultures; and in particular for controlling Alopecurus myosuroides in cereal and/or rapeseed cultures.

The term crop plants also includes those plants which have been modified by breeding, mutagenesis or methods, including the biotechnological agricultural products which are on the market or in the process of being developed. Genetically modified plants are plants whose genetic material has been modified in a manner which does not occur under natural conditions by hybridizing, mutations or natural recombination (i.e. recombination of the genetic material). Here, one or more genes will, as a rule, be integrated into the genetic material of the plant in order to improve the plant's properties. Such recombinant modifications also comprise posttranslational modifications of proteins, oligo- or polypeptides, for example by means of glycosylation or binding polymers such as, for example, prenylated, acetylated or farnesylated residues or PEG residues.

The microcapsules and the composition of the invention are useful for combating undesired vegetation. For this purpose, the microcapsules or the composition may be applied as such or are preferably applied after dilution with water. Preferably, for various purposes of end user application, a so-called aqueous spray-liquor is prepared by diluting the microcapsules or the compositions of the present invention with water, e.g. tap water. The spray-liquors may also comprise further constituents in dissolved, emulsified or suspended form, for example fertilizers, active substances of other groups of herbicidal or growth-regulatory active substances, further active substances, for example active substances for controlling animal pests or phytopathogenic fungi or bacteria, furthermore mineral salts which are employed for alleviating nutritional and trace element deficiencies, and non-phytotoxic oils or oil concentrates. These agents can be admixed with the microcapsules or compositions according to the invention in a weight ratio of 1:100 to 100:1, preferably 1:10 to 10:1. As a rule, these constituents are added to the spray mixture before, during or after dilution of the compositions according to the invention. The microcapsules or the composition according to the invention are usually applied from a predosage device, a knapsack sprayer, a spray tank, a spray plane, or an irrigation system. Usually, 20 to 2000 liters, preferably 50 to 400 liters, of the ready-to-use spray liquor are applied per hectare of agricultural useful area.

The microcapsules or the composition of the invention can be applied by the preemergence or the post-emergence method. If one of the active compounds is less well tolerated by certain crop plants, application techniques may be employed where the herbicidal compositions are sprayed, with the aid of the spraying apparatus, in such a way that the leaves of the sensitive crop plants ideally do not come into contact with them, while the active substances reach the leaves of undesired plants which grow underneath, or the bare soil surface (post-directed, lay-by).

Various types of oils, wetters, adjuvants, fertilizer, or micronutrients, and further pesticides (e.g. herbicides, insecticides, fungicides, growth regulators, safeners) may be added to the compositions comprising them as premix or, if appropriate not until immediately prior to use (tank mix). These agents can be admixed with the compositions according to the invention in a weight ratio of 1:100 to 100:1, preferably 1:10 to 10:1.

The microcapsules or composition of the invention are generally applied in such amounts that the amounts of cinmethylin applied are, depending on the kind of effect desired, from 0.001 to 2 kg per ha, preferably from 0.005 to 2 kg per ha, more preferably from 0.05 to 0.9 kg per ha, in particular from 0.05 to 0.6 kg per ha.

The microcapsules of the present invention have a well-balanced volatility and release profile. On the one side the volatility of cinmethylin encapsulated therein is decreased, but just to an extent which still allows a sufficient release thereof, so that a sufficient herbicidal activity is still obtained. The microcapsules and compositions containing them are stable during storage for a long time, even at a wide temperature range, even when cinmethylin is present in high concentrations in the composition and even when the composition contains (outside the microcapsules) further pesticides which are not compatible with cinmethylin. Especially sediment formation, agglomeration, crystallization and syneresis as observed with compositions containing "naked" cinmethylin which is not comprised in microcapsules and further herbicides do not occur.

The invention is now further illustrated by the following examples and figures.

FIGURES

FIG. 1 shows the amount of cinmethylin found in the water trays 0, 2 and 4 days after treatment of the field with the cinmethylin EC formulation; expressed as percentage of the applied amount.

FIG. 2 shows the amount of cinmethylin found in the water trays 0, 2 and 4 days after treatment of the field with the cinmethylin CS formulation of the invention; expressed as percentage of the applied amount.

EXAMPLES

Figure 1:
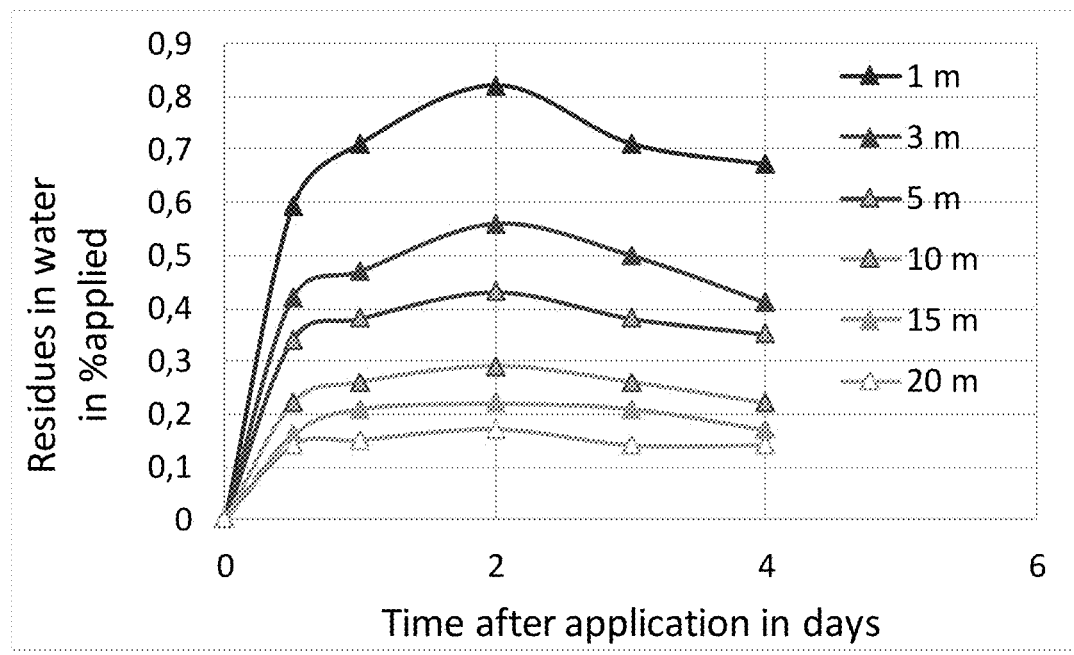
FIGS. 1 and 2 show the results of the wind tunnel test of example 3.

In the examples, cinmethylin refers to the racemic mixture (±)-2-exo-(2-methylbenzyloxy)-1-methyl-4-isopropyl-7-oxabicyclo[2.2.1]heptane.

1. Synthetic Examples—Preparation of Cinmethylin Microcapsules

Lupranat® M20 S: a PMDI with an NCO content of 31.5%, a viscosity of 210 mPa·s at 25° C. (determined according to DIN 53018) and an average NCO functionality of 2.7; from BASF SE Reax® 88B sodium salt of a chemically modified low molecular weight kraft lignin polymer solubilized by five sulfonate groups; a dispersant from MeadWestvaco Corporation, molecular weight about 3000 g/mol, water-soluble, CAS 68512-34-5

Naphth.sulf.: sodium salt of naphthalene sulfonate condensate

Rhodopol® G xanthan gum thickener from Rhodia

Acticide® MBS biocide from Thor GmbH; water based formulation of 2-methylisothiazolin-3-one and 1,2-benzisothiazolin-3-one Silicon SRE-PFL antifoam from Wacker Preparation of Cinmethylin Microcapsules An aqueous phase was prepared by mixing a lignosulfonate (Reax® 88B) and magnesium-sulfate heptahydrate with 400 g of water under stirring at room temperature.

An oily phase was prepared by mixing cinmethylin and Lupranat® M 20 S (a PMDI from BASF).

The oily phase was poured into the aqueous phase. The mixture was homogenized by first mixing with an Ultraturrax for 60 s, then at 14000 rpm for 15 s, then mixing with a Viskojet at 200 rpm. Hexamethylene diamine (hexane-1,6-diamine) was added at a rate of 15 ml/min. The mixture was stirred at 250 rpm for 2 h at 20° C., then the sodium salt of naphthalene sulfonate condensate, Rhodopol® G (a xanthan gum thickener from Rhodia) and Acticide® MBS (a biocide from Thor GmbH), dispersed in 10% of water, were added and stirring was continued for a further hour at 280 rpm. Acetic acid was added under stirring at 350 rpm until pH 7-8 was reached. Then 2 g of Wacker-Silicon SRE-PFL (an antifoam from Wacker) was rapidly added. Finally water was added to give 1 L of suspension. The obtained mixture was filtered over a 150 μm sieve.

The proportions of the components are given in table 1.

TABLE 1

|  | Example 1 Amount [g/L] | Example 2 Amount [g/L] | Example 3 Amount [g/L] | Example 4 Amount [g/L] |
| --- | --- | --- | --- | --- |
| Cinmethylin | 400 | 400 | 450 | 450 |
| PMDI | 5.0 | 4.5 | 5.6 | 5.1 |
| Hexane-1,6-diamine | 1.88 | 1.88 | 2.1 | 2.1 |
| Reax ® 88B | 12 | 12 | 13.5 | 13.5 |
| Naphth.sulf. | 6 | 6 | 6.0 | 6 |
| Magnesiumsulfate•7H$_2$O | 110 | 110 | 110 | 110 |
| Xanthan gum | 1 | 1 | 1 | 1 |
| Silicon antifoam | 0.6 | 0.6 | 0.6 | 0.6 |
| Biocide | 2.0 | 2.0 | 2.0 | 2.0 |
| Water | ad 1.0 L | ad 1.0 L | ad 1.0 L | ad 1.0 L |
| Reaction temperature | 20 | 20 | 20 | 20 |

All examples resulted in discrete microcapsule suspensions (CS) with a microcapsule diameter ($d_{50}$) of 1-30 μm.

2. Volatility/Release Tests

The amount of released active ingredient over time was determined as follows: First a 10% solution of Poloxamer 335 (Pluronic PE 10500) was prepared which was adjusted to pH 5 with acetic acid. This solution acted as receiver solution for the non-encapsulated active or the released active. To 250 ml of the receiver solution 125 mg of the microcapsule suspension was added. The solution was stirred and at defined time points, a sample was drawn. A 0.2 μm Teflon filter was used to remove the remaining microcapsules. In the filtrate, the pesticide was determined via reverse phase HPLC and normalized in a way that the entire amount of the pesticide would account for 100%. This would have been found for example if no encapsulation would have taken place (like in an EC formulation) or all of the pesticide would have been released.

Release Rates [%]:

TABLE 2

|  | 10 min | 5 h | 24 h | 3 d | 7 d |
| --- | --- | --- | --- | --- | --- |
| Experiement 1 | 3 | 9 | 21 | 43 | 73 |
| Experiement 2 | 4 | 32 | 40 | 68 | 90 |
| Experiement 3 | 4 | 37 | 44 | 72 | 92 |
| Experiement 4 | 4 | 44 | 55 | 91 | 93 |

3. Residues in Surface Water—Wind Tunnel Tests

This test serves as a model for the determination of the contamination of surface water with volatile pesticides.

The field used in the wind tunnel test had an area of 100 m$^2$ (4 m×25 m). The field was overgrown with local grasses (mostly weeds). To the field either an EC formulation of cinmethylin (comparison) or the CS composition according to example 1 was applied; in both cases in a rate of 500 g of cinmethylin per hectare. 26 synchronized fans created a constant, slow wind along the length of the tunnel. Beside the test field stainless steel trays with each 25 l of water acted as deposition area. The trays had a distance from the applied field of 1, 3, 5, 10, 15 and 20 m, respectively. The amount of cinmethylin in the trays was determined over time via GC. The experiment with the EC formulation acted as a comparison.

Figure 2:
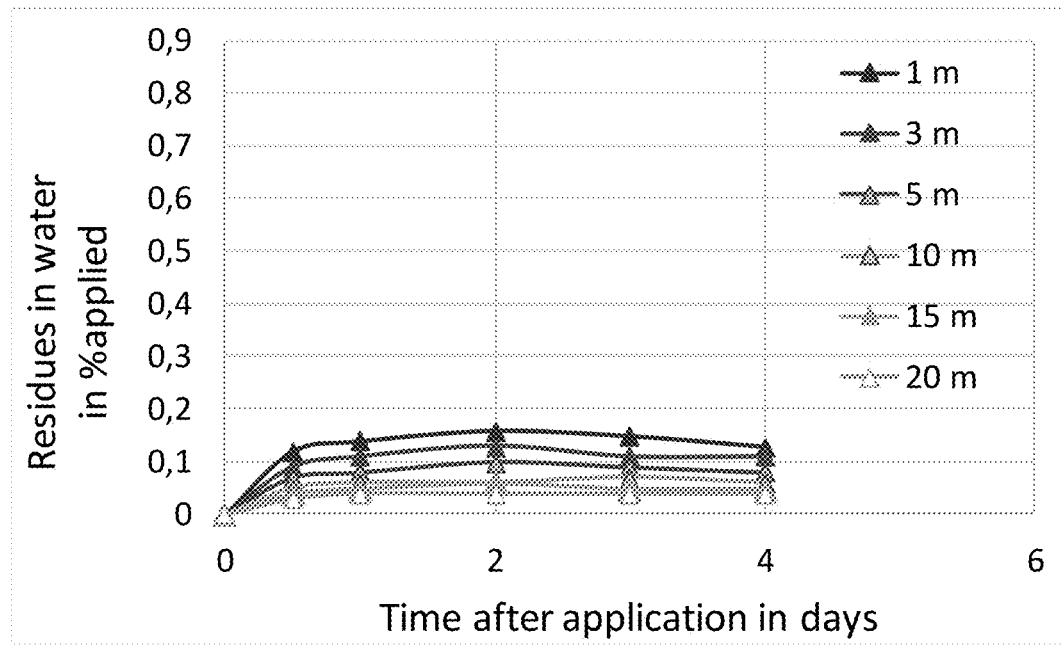

The results are shown in FIGS. 1 and 2. FIG. 1 shows the amount of cinmethylin found in the water trays 0, 2 and 4 days after treatment of the field with the cinmethylin EC formulation; expressed as percentage of the applied amount. FIG. 2 shows the amount of cinmethylin found in the water trays 0, 2 and 4 days after treatment of the field with the cinmethylin CS formulation of the invention; expressed as percentage of the applied amount.

As can be seen, the application of cinmethylin as the CS formulation of the invention resulted in a significantly lower amount of active compound in the trays, as compared to the amount found after the application of cinmethylin as an EC formulation; the amount being decreased by a factor of 3-5. The microcapsules of the invention thus effectively reduce the volatility and undesired distribution of cinmethylin.

4. Herbicidal Activity

The effects on the growth of undesirable plants of the herbicidal compositions comprising microcapsules which were obtained in the above examples was demonstrated by the following greenhouse experiments:

The test plants were seeded in plastic containers in sandy loamy soil containing 5% of organic matter. For the pre-emergence treatment, the compositions were applied directly after sowing by means of finely distributing nozzles at a use rate of 250 g active ingredient/ha. The containers were irrigated gently to promote germination and growth and subsequently covered with transparent plastic hoods until the plants had rooted. This cover caused uniform germination of the test plants unless this was adversely affected by the active compounds. The plants were cultivated according to their individual requirements at 10-25° C. and 20-35° C. In the following experiments, the herbicidal activity for the individual herbicidal compositions was assessed 20 days after treatment. The results are summarized in table 4. The evaluation for the damage on undesired weeds caused by the compositions was carried out using a scale from 0 to 100%, compared to the untreated control plants. Here, 0 means no damage and 100 means complete destruction of the plants.

For comparison, cinmethylin was used as an emulsion concentrate with an active ingredient concentration of 750 g/l; use rate 250 g active ingredient/ha.

The plants used in the greenhouse experiments belonged to the following species:

| EPPO Code | Scientific name |
|---|---|
| ALOMY | Alopecurus myosuroides |
| LOLRI | Lolium rigidum |
| BROST | Bromus sterilis |
| AVEFA | Avena fatua |
| MATIN | Tripleurospermum inodorum (Matricaria inodora) |
| PAPRH | Papaver rhoeas |
| GALAP | Galium aparine |

TABLE 4

| | Cinmethylin as EC* | Example 1 | Example 2 | Example 3 | Example 4 |
|---|---|---|---|---|---|
| ALOMY | 100 | 100 | 100 | 100 | 100 |
| LOLRI | 100 | 90 | 95 | 100 | 100 |
| BROST | 100 | — | 90 | 75 | 80 |
| AVEFA | 95 | — | — | 75 | 85 |
| MATIN | 99 | 74 | 75 | 88 | 90 |
| PAPRH | 80 | 65 | 85 | — | 70 |
| GALAP | 85 | 85 | — | 85 | 85 |

*Comparison

As the results show, the herbicidal activity of the cinmethylin microcapsules of the invention is good.

We claim:

1. Microcapsules comprising a core, wherein the core comprises cinmethylin, and a shell, wherein the shell comprises a polyurea material which comprises a polyaddition product of (1) polymeric methylene diphenyl diisocyanate having an average functionality in the range of 2.0 to 4.0 and (2) an aliphatic diamine of the formula $H_2N—(CH_2)_p—NH_2$, wherein p is 6;
where a weight ratio of cinmethylin and the polyurea material of the shell is from 40:1 to 70:1; and
where an overall weight ratio of cinmethylin and the polymeric methylene diphenyl diisocyanate present in the shell in polymerized form is from 50:1 to 120:1.

2. The microcapsules according to claim 1, where an average particle size $d_{50}$ of the microcapsules, as determined according to ISO 13320, Particle Size Analysis-Laser Diffraction Methods, December, 1, 2009, is from 0.5 to 100 μm.

3. A composition comprising microcapsules as defined in claim 1 and a dispersing medium.

4. The composition according to claim 3, where the dispersing medium is an aqueous medium and the composition is an aqueous dispersion.

5. The composition according to claim 3, containing the microcapsules in an amount of from 10 to 70% by weight, based on the total weight of the composition.

6. The composition according to claim 3, further comprising at least one ingredient selected from the group consisting of a surfactant, a dispersing agent, an emulsifier, a wetting agent, an adjuvant, an inorganic salt, a solubilizer, a penetration enhancer, a protective colloid, an adhesion agent, a thickener, a humectant, an antifoam, an antifreeze agent, a stabilizer, an antimicrobial agent, a pigment, a colorant, a buffer, a tackifier, a binder, and combinations thereof.

7. A composition comprising
(i) microcapsules as defined in claim 1;
(ii) at least one herbicide different from cinmethylin; and
(iii) optionally a dispersing medium.

8. The composition according to claim 7, where the at least one herbicide different from cinmethylin is selected from the group consisting of:
(ii.1) herbicides from the group of lipid biosynthesis inhibitors, which are in turn selected from the group consisting of:

ACC-herbicides selected from the group consisting of alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); and 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides selected from the group consisting of benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

(ii.2) herbicides from the group of ALS inhibitors, which are in turn selected from the group consisting of:

sulfonylureas selected from the group consisting of amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones selected from the group consisting of imazamethabenz, imazamethabenz-methyl, imazamox, imazapic, imazapyr, imazaquin and imazethapyr, triazolopyrimidine herbicides and sulfonanilides selected from the group consisting of cloransulam, cloransulam-methyl, diclosulam, flumetsulam, florasulam, metosulam, penoxsulam, pyrimisulfan and pyroxsulam, pyrimidinylbenzoates selected from the group consisting of bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), and N-(4-bromophenyl)-2-[(4,6-dimethoxy-2-pyrimidinyl)oxy]benzenemethanamine (CAS 420138-01-8), sulfonylaminocarbonyl-triazolinone herbicides selected from the group consisting of flucarbazone, flucarbazone-sodium, propoxycarbazone, propoxycarbazone-sodium, thiencarbazone and thiencarbazone-methyl; and triafamone;

(ii.3) herbicides from the group of the photosynthesis inhibitors, which are in turn selected from the group consisting of:

amicarbazone, inhibitors of the photosystem II selected from the group consisting of triazine herbicides, in turn selected from the group consisting of chlorotriazine, triazinones, triazindiones, methylthiotriazines and pyridazinones in turn selected from the group consisting of ametryn, atrazine, chloridazone, cyanazine, desmetryn, dimethametryn, hexazinone, metribuzin, prometon, prometryn, propazine, simazine, simetryn, terbumeton, terbuthylazin, terbutryn and trietazin, aryl urea herbicides selected from the group consisting of chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates selected from the group consisting of desmedipham, karbutilat, phenmedipham and phenmedipham-ethyl, nitrile herbicides selected from the group consisting of bromofenoxim, bromoxynil and its salts and esters, and ioxynil and its salts and esters, uraciles selected from the group consisting of bromacil, lenacil and terbacil, bentazon and bentazon-sodium, pyridate, pyridafol, pentanochlor, and propanil; and inhibitors of the photosystem I selected from the group consisting of diquat, diquat-dibromide, paraquat, paraquat-dichloride and paraquat-dimetilsulfate, (ii.4) herbicides from the group of protoporphyrinogen-IX oxidase inhibitors, which are in turn selected from the group consisting of:

acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (S-3100) (CAS 353292-31-6); S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoro-methylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate (CAS 948893-00-3), and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-02-4);

(ii.5) herbicides from the group of the bleacher herbicides, which are in turn selected from the group consisting of:

PDS inhibitors selected from the group consisting of beflubutamid, diflufenican, fluri done, flurochloridone, flurtamone, norflurazon, picolinafen, and 4-(3-trifluoromethylphenoxy)-2-(4-trifluoromethylphenyl)pyrimidine (CAS 180608-33-7), HPPD inhibitors selected from the group consisting of benzobicyclon, benzofenap, bicyclopyrone, clomazone, fenquinotrione, isoxaflutole, mesotrione, oxotrione (CAS 1486617-21-3), pyrasulfotole, pyrazolynate, pyrazoxyfen, sulcotrione, tefuryltrione, tembotrione, tolpyralate and topramezone;

aclonifen, amitrole flumeturon and 2-chloro-3-methylsulfanyl-N-(1-methyltetrazol-5-yl)-4-(trifluoromethyl)benzamide;

(ii.6) herbicides from the group of EPSP synthase inhibitors, which are in turn selected from the group consisting of:

glyphosate, glyphosate-isopropylammonium, glyposate-potassium and glyphosate-trimesium (sulfosate);

(ii.7) herbicides from the group of the glutamine synthase inhibitors, which are in turn selected from the group consisting of:

bilanaphos (bialaphos), bilanaphos-sodium, glufosinate, glufosinate-P and glufosinate-ammonium;

(ii.8) asulam as a DHP synthase inhibitor herbicide;

(ii.9) herbicides from the group of the mitosis inhibitors, which are in turn selected from the group consisting of:

compounds of group K1 selected from the group consisting of dinitroanilines in turn selected from the group consisting of benfluralin, butralin, dinitramine, ethalfluralin, fluchloralin, oryzalin, pendimethalin, prodiamine and trifluralin, phosphoramidates selected from the group consisting of amiprophos, amiprophos-methyl, and butamiphos;

benzoic acid herbicides selected from the group consisting of chlorthal and chlorthal-dimethyl, pyridines selected from the group consisting of dithiopyr and thiazopyr, and benzamides selected from the group consisting of propyzamide and tebutam; and compounds of group K2 selected from the group consisting of carbetamide, chlorpropham, flamprop, flamprop-isopropyl, flamprop-methyl, flamprop-M-isopropyl, flamprop-M-methyl and propham, (ii.10) herbicides from the group of the VLCFA inhibitors, which are in turn selected from the group consisting of:

chloroacetamides selected from the group consisting of acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides selected from the group consisting of flufenacet and mefenacet, acetanilides selected from the group consisting of diphenamid, naproanilide, napropamide and napropamide-M, fentrazamide; and other herbicides selected from the group consisting of anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9

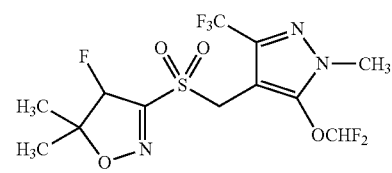

II.1

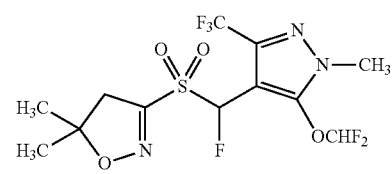

II.2

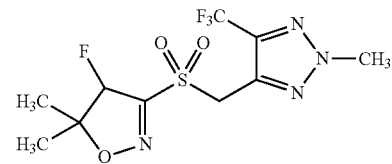

II.3

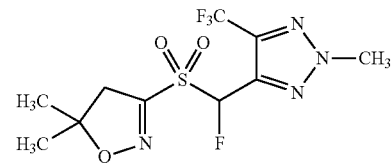

II.4

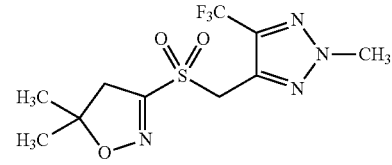

II.5

-continued

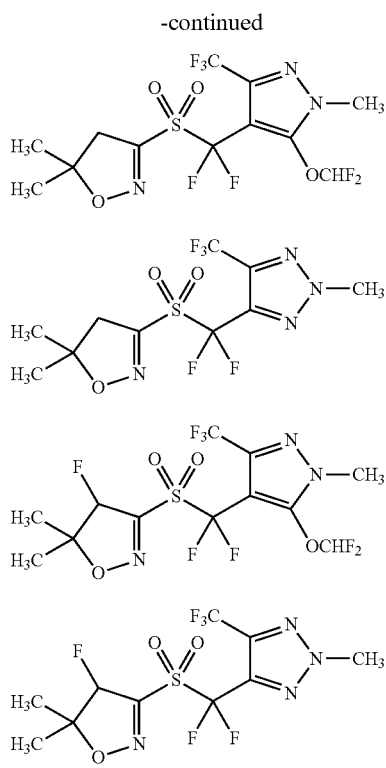

II.6

II.7

II.8

II.9

(ii.11) herbicides from the group of the cellulose biosynthesis inhibitors, which are in turn selected from the group consisting of:
chlorthiamid, dichlobenil, flupoxam, indaziflam, isoxaben, triaziflam and 1-cyclohexyl-5-pentafluorophenyloxy-1λ$^4$-1,2,4,6-thiatriazin-3-ylamine (CAS 175899-01-1);

(ii.12) herbicides from the group of decoupler herbicides, which are in turn selected from the group consisting of:
dinoseb, dinoterb and DNOC and its salts;

(ii.13) herbicides from the group of auxinic herbicides, which are in turn selected from the group consisting of:
2,4-D and its salts and esters, 2,4-DB and its salts and esters, aminocyclopyrachlor and its salts and esters, aminopyralid and its salts, aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, flopyrauxifen, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, 4-amino-3-chloro-6-(4-chloro-2-fluoro-3-methoxyphenyl)-5-fluoropyridine-2-carboxylic acid, benzyl 4-amino-3-chloro-6-(4-chloro-2-fluoro-3-methoxyphenyl)-5-fluoropyridine-2-carboxylate (CAS 1390661-72-9) and 4-amino-3-chloro-5-fluoro-6-(7-fluoro-1H-indol-6-yl)picolinic acid;

(ii.14) herbicides from the group of the auxin transport inhibitors, which are in turn selected from the group consisting of:
diflufenzopyr, diflufenzopyr-sodium, naptalam and naptalam-sodium; and (ii.15) other herbicides selected from the group consisting of:
bromobutide, chlorflurenol, chlorflurenol-methyl, cumyluron, cyclopyrimorate and its salts and esters, dalapon, dazomet, difenzoquat, difenzoquat-metilsulfate, dimethipin, DSMA, dymron, endothal and its salts, etobenzanid, flurenol, flurenol-butyl, flurprimidol, fosamine, fosamine-ammonium, indanofan, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine and tridiphane.

9. The composition according to claim 8, where the at least one herbicide different from cinmethylin is selected from the group consisting of quinmerac, picolinafen, dimethenamid, dimethenamid-P, imazamox, diflufenican, flufenacet, pendimethalin, pyroxasulfone, sulfonylureas selected from the group consisting of amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, and aminopyralid and its salts.

10. The composition according to claim 9, where the at least one herbicide different from cinmethylin is selected from the group consisting of quinmerac, picolinafen, dimethenamid, dimethenamid-P, diflufenican, flufenacet and pendimethalin.

11. A method for preparing microcapsules as defined in claim 1, comprising polymerizing the polymeric methylene diphenyl diisocyanate and the aliphatic diamine in the presence of cinmethylin, where cinmethylin and the polymeric methylene diphenyl diisocyanate are used in an overall weight ratio of from 50:1 to 120:1.

12. The method according to claim 11, comprising following steps:
(a) providing an aqueous phase containing water, further containing a dispersant and/or a surfactant, and optionally containing at least one further ingredient selected from the group consisting of emulsifier, wetting agent, further adjuvant, inorganic salt, solubilizer, penetration enhancer, protective colloid, adhesion agent, thickener, humectant, antifoam, antifreeze agent, stabilizer, antimicrobial agent, pigment, colorant, buffer, tackifier and binder;
(b) providing an oily phase containing the cinmethylin and the polymeric methylene diphenyl diisocyanate, where the oily phase contains the cinmethylin and the polymeric methylene diphenyl diisocyanate in an overall weight ratio of from 50:1 to 120:1;
(c) mixing the aqueous phase of step (a) and the oily phase of step (b) to form an emulsion;
(d) adding the aliphatic diamine to the mixture obtained in step (c) and optionally heating the reaction either during the addition of the aliphatic diamine or after the addition of the aliphatic diamine or both;

(e) optionally adding at least one ingredient selected from the group consisting of emulsifier, wetting agent, further adjuvant, solubilizer, penetration enhancer, protective colloid, adhesion agent, thickener, humectant, antifoam, antifreeze agent, stabilizer, antimicrobial agent, pigment, colorant, buffer, tackifier and binder to the mixture obtained in step (d);

(f) optionally adjusting the pH to a desired value; and (g) optionally bringing the mixture obtained in step (d), (e) or (f) to a desired concentration.

13. The method according to claim 12, where the dispersant used in step (a) is a sulfonate dispersant selected from the group consisting of lignosulfonate, naphthalene sulfonate formaldehyde condensate and mixtures thereof.

14. The method according to claim 11, where the aliphatic diamine and the polymeric methylene diphenyl diisocyanate are used in a ratio such that the molar ratio of all primary amino groups $NH_2$ contained in the aliphatic amine and all isocyanate groups contained in the polymeric methylene diphenyl diisocyanate is from 2.5:1 to 1:1.5.

15. The microcapsules according to claim 1, where:
the weight ratio of cinmethylin and the polyurea material of the shell is from 40:1 to 65:1; and
the overall weight ratio of cinmethylin and the polymeric methylene diphenyl diisocyanate present in the shell in polymerized form is from 50:1 to 90:1.

16. The microcapsules according to claim 1, where;
the overall weight ratio of cinmethylin and the polymeric methylene diphenyl diisocyanate present in the shell in polymerized form is from 60:1 to 100:1.

17. Microcapsules comprising a core, wherein the core comprises cinmethylin, and a shell, wherein the shell comprises a polyurea material which comprises a polyaddition product of (1) polymeric methylene diphenyl diisocyanate having an average functionality in the range of 2.0 to 4.0 and (2) an aliphatic diamine of the formula $H_2N$—$(CH_2)_p$—$NH_2$, wherein p is 6;
where a weight ratio of cinmethylin and the polyurea material of the shell is from 40:1 to 80:1; and
where an overall weight ratio of cinmethylin and the polymeric methylene diphenyl diisocyanate present in the shell in polymerized form is from 50:1 to 120:1.

* * * * *